United States Patent
Mahajan

(10) Patent No.: US 6,403,860 B1
(45) Date of Patent: Jun. 11, 2002

(54) KU80 HOMOLOGUE AND USES THEREOF

(75) Inventor: Pramod B. Mahajan, Urbandale, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/494,810

(22) Filed: Jan. 31, 2000

Related U.S. Application Data

(60) Provisional application No. 60/126,214, filed on Mar. 25, 1999.

(51) Int. Cl.$^7$ .......................... C12N 15/09; C12N 15/29; C12N 15/82; A01H 5/00

(52) U.S. Cl. ........................ 800/278; 800/298; 800/295; 800/306; 800/312; 800/314; 800/322; 800/320; 800/320.1; 800/320.2; 800/320.3; 435/69.1; 435/419; 435/468; 435/320.1; 536/23.2; 536/23.6; 536/24.1

(58) Field of Search .............................. 800/278, 286, 800/320, 320.1, 320.2, 36.3, 306, 314, 312, 322, 295, 298; 435/69.1, 320.1, 419, 468; 536/23.2, 23.6, 24.1, 24.5

(56) References Cited

FOREIGN PATENT DOCUMENTS

| WO | WO 98/05763 | 2/1998 | ........... C12N/15/00 |
|---|---|---|---|
| WO | WO 00/12716 | 3/2000 | ........... C12N/15/19 |

OTHER PUBLICATIONS

Lazar et al, "Transforming Growth Factor x:Mutation of Aspartic Acid 47 and Leucine 48 Results in Different Biological Activities", Mar. 1988, Molecular and Cellular Biology vol. 8 No. 3, pp. 1247–1252.*
Broun et al, "Catalytic Plasticity of Fatty Acid Modification Enzymes Underlying Chemical Diversity of Plant Lipids", Nov. 1998, Science vol. 282, pp. 1315–1317.*
Bork, "Powers and Pitfalls in Sequence Analysis: The 70% Hurdle", Genome Research vol. 10: 398–400.*
Errami et al., "Ku86 Defines the Genetic Defect and Restores X–Ray Resistance and V(D)J Recombination to Complementation Group 5 Hamster Cell Mutants", *Mol. Cell Bio.* 16(4):1519–1526 (1996).
Falzon et al., "The nucleotide sequence of a mouse cDNA encoding the 80 kDa subunit of the Ku (p70/p80) autoantigen" *Nucleic Acids Research* 20(14):3784 (1992).
Ludwig et al., "Ku80 gene expression is SP1–dependent and sensitive to CpG methylation within a novel *cis* element", *Gene* 199:181–194 (1997).
Frit et al., Ku70/Ku80 Protein Complex Inhibits the Binding of Nucleotide Excision Repair Proteins on Linear DNA in Vitro *J. Mol. Biol.* 284:963–973 (1998).

Database EMBL Nucleotide and Protein Sequences, HINXTON GB AC=AW066150.687006H02.y1 687—Early embryo from Delaware Zea mays cDNA, mRNA sequence. EST Oct. 18, 1999.
Troelstra, C. and Jaspers, N.G.J., 1994, *Current Biology*, 4(12): 1149–1151, "Ku starts at the end".
Taccioli, et al., 1994, *Science*, 265: 1442–1445, "Ku80: Product of the XRCC5 Gene and Its Role in DNA Repair and V(D)J Recombination".
Cary, et al., 1998, *Nucleic Acids Res.*, 26(4): 974–979, "A central region of Ku80 mediates interaction with Ku70 in vivo".
Osipovich, et al., 1997, *J. Biological Chem.*, 272(43): 27259–27265, "Defining the Minimal Domain of Ku80 for Interaction with Ku70*".
Wang, et al., 1998, *J. Biological Chem.*, 273(47): 31068–31074, "A Model for Ku Heterodimer Assembly and Interaction with DNA".
Jackson, S. and Jeggo, P., 1995, *TIBS 20*, 412–415, "DNA double–strand repair and V(D)J recombination: involvement of DNA–PK".
Shinohara, A. and Ogawa, T., 1995, *TIBS 20*, 387–391, "Homologous recombination and the roles of double–strand breaks".
Chu, G., 1997, *J. Biological Chem.*, 272(39):24097–24100, "Double Strand Break Repair*".
Feldmann, et al., *J. Biological Chem.*, 271(44): 27765–27769, "HDF2, the Second Subunit of the Ku Homologue from *Saccharomyces cerevisiae*\*".
Yaneva, M. and Arnett, F.C., 1989, *Clin. exp. Immunol.*, 76: 366–372, "Antibodies against Ku protein in sera from patients with autoimmune diseases".
Jacoby, D., and Wensink, P., 1994, *J. Biological Chem.*, 269(15): 11484–11491, "Yolk Protein Factor 1 Is a Drosophila Homolog of Ku, the DNA–binding Subunit of a DNA–dependent Protein Kinase from Humans".
Polotnianka, et al., 1998, *Current Biology*, 8(14): 831–834, "The yeast Ku heterodimer is essential for protection of the telomere against nucleolytic and recombinational activities".
Roth, et al., 1995, *Current Biology*, 5(5): 496–499, "How to make ends meet".
Boulton, S. and Jackson S., 1998, *The EMBO Journal*, 17(6): 1819–1828, "Components of the Ku–dependent non–homologous end–joining pathway are involved in telomeric length maintenance and telomeric silencing".

(List continued on next page.)

*Primary Examiner*—Phuong T. Bui
*Assistant Examiner*—Medina A. Ibrahim
(74) *Attorney, Agent, or Firm*—Pioneer Hi-Bred International, Inc.

(57) ABSTRACT

The invention provides isolated Ku80 nucleic acids and their encoded proteins. The present invention provides methods and compositions relating to altering Ku80 levels in plants. The invention further provides recombinant expression cassettes, host cells, transgenic plants, and antibody compositions.

14 Claims, No Drawings

OTHER PUBLICATIONS

Yoo, S. and Dynan, W., 1998, *Biochemistry*, 37: 1336–1343, "Characterization of the RNA Binding Properties of Ku Protein".

Mimori, et al., 1986, *J. Biological Chem.*, 261(5): 2274–2278, "Characterization of the DNA–binding Protein Antigen Ku Recognized by Autoantibodies from Patients with Rheumatic Disorders*".

Lindahl, et al., 1995, *TIBS 20*, 405–411, "Post–translational modification of poly(ADP–ribose) polymerase induced by DNA strand breaks".

Anderson, et al., 1992, *Critical Review in Eukaryotic Gene Exp.*, 2(4): 283–314, "The Nuclear Serine/Threonine Protein Kinase DNA–PK".

DVIR, et al., 1992, *Proc. Natl. Acad. Sci.*, 89: 11920–11924, "Ku autoantigen is the regulatory component of a template–associated protein kinase that phosphorylates RNA polymerase II".

* cited by examiner

SEQUENCE LISTING

```
<160> NUMBER OF SEQ ID NOS:  7

<210> SEQ ID NO 1
<211> LENGTH: 2419
<212> TYPE: DNA
<213> ORGANISM: Zea mays
<220> FEATURE:
<221> NAME/KEY: CDS
<222> LOCATION: (136)...(2178)

<400> SEQUENCE: 1
gacccacgcg tccgctcgac cgtcagtcaa ttcctgcacc aggcgttggg c gggttttat     60 ggggcagca taaaagcctc ttcggttctt ccctagctc tgcctcgcgg c aagtccccc    120 tccgctacgt cgcc atg gct cgc aac agg gaa gtg gtg att ttg ctg ttg    171
              Met  Ala Arg Asn Arg Glu Val Val Ile Leu Leu Leu
                1               5                  10 gat gtt ggg cct tcg atg cat gga gtg ctg c ta gag gtg aag aac gta    219
Asp Val Gly Pro Ser Met His Gly Val Leu L eu Glu Val Lys Asn Val
```

|  |  |
|---|---|
| tgc ttg act ctt gtg cat aag aag cta gtt t at aac agg agc gat gaa<br>Cys Leu Thr Leu Val His Lys Lys Leu Val Tyr Asn Arg Ser Asp Glu<br>30               35               40 | 267 |
| gtt ggt att gtc ctc ttt ggt act aaa gga a ca tgc aat gag ctt gca<br>Val Gly Ile Val Leu Phe Gly Thr Lys Gly Thr Cys Asn Glu Leu Ala<br>45               50               55               60 | 315 |
| aag gac att ggg ggc tat aag cat gtg acg g tc ata cat gat att aaa<br>Lys Asp Ile Gly Gly Tyr Lys His Val Thr Val Ile His Asp Ile Lys<br>               65               70               75 | 363 |
| gtt gta gat gaa gga acg gca cag gct ctg c aa aac ctt cca tta gga<br>Val Val Asp Glu Gly Thr Ala Gln Ala Leu Gln Asn Leu Pro Leu Gly<br>               80               85               90 | 411 |
| tct gcc cct ggt gat ttt ctg gat tct att g tt gtt ggc ttg gat atg<br>Ser Ala Pro Gly Asp Phe Leu Asp Ser Ile Val Val Gly Leu Asp Met<br>               95              100             105 | 459 |
| gtg att agg aaa ttt ggt att acc aaa ggg a ag cgg cgg ctc tgt cta<br>Val Ile Arg Lys Phe Gly Ile Thr Lys Gly Lys Arg Arg Leu Cys Leu<br>110             115            120 | 507 |
| atc act agt gca caa gaa ctg tta aga gat c cg cct gag ggg acc aaa<br>Ile Thr Ser Ala Gln Glu Leu Leu Arg Asp Pro Pro Glu Gly Thr Lys<br>125             130              135             140 | 555 |
| gaa gat caa gtg gac acc att gca gac atg t tg aaa aaa cac aat atc<br>Glu Asp Gln Val Asp Thr Ile Ala Asp Met Leu Lys Lys His Asn Ile<br>              145              150             155 | 603 |
| aag atg gag tgc att att ttc aga gaa ccg g ga gtg cat cat aat gat<br>Lys Met Glu Cys Ile Ile Phe Arg Glu Pro Gly Val His His Asn Asp<br>              160              165             170 | 651 |
| ata atg gaa gaa aat gac cga cta ttg cat c ag ttc aga aat cga tca<br>Ile Met Glu Glu Asn Asp Arg Leu Leu His Gln Phe Arg Asn Arg Ser<br>175             180            185 | 699 |
| gta gca aag gta att cag gtt gac aac cca a ca tca ctg ttg ggt gct<br>Val Ala Lys Val Ile Gln Val Asp Asn Pro Thr Ser Leu Leu Gly Ala<br>190             195              200 | 747 |
| ctc aag aca aga aat gtg ctc cca gtt acc g tt ttc agg gga gac ctg<br>Leu Lys Thr Arg Asn Val Leu Pro Val Thr Val Phe Arg Gly Asp Leu<br>205             210            215             220 | 795 |
| gaa gtg aac tcc aat ttt aaa ata aag gtg t gg gta tat aag aaa aca<br>Glu Val Asn Ser Asn Phe Lys Ile Lys Val Trp Val Tyr Lys Lys Thr<br>              225              230             235 | 843 |
| gct gag gaa aaa ttc ccc act ttg aag aag t at tcg gac aaa gct cct<br>Ala Glu Glu Lys Phe Pro Thr Leu Lys Lys Tyr Ser Asp Lys Ala Pro<br>              240              245             250 | 891 |
| cca agt gat aaa ttt gct tct cat gaa gtc a aa gtt gat tat gag tac<br>Pro Ser Asp Lys Phe Ala Ser His Glu Val Lys Val Asp Tyr Glu Tyr<br>255             260            265 | 939 |
| aag agt gtt gtt gag cca gac aaa gtt gtt c ca cca gac cag agg att<br>Lys Ser Val Val Glu Pro Asp Lys Val Val Pro Pro Asp Gln Arg Ile<br>270             275            280 | 987 |
| aag ggg tat ctc tat ggt cct caa gtt att c ct gta tca aat gct gaa<br>Lys Gly Tyr Leu Tyr Gly Pro Gln Val Ile Pro Val Ser Asn Ala Glu<br>285             290            295             300 | 035 |
| tgg gag gca gtc aag ttc aag cca gag aaa g gt gtg aag ctt cta gga<br>Trp Glu Ala Val Lys Phe Lys Pro Glu Lys Gly Val Lys Leu Leu Gly<br>              305              310             315 | 083 |
| ttt aca gat aga tcc agc gta cca cgg cac c aa ttt atg aaa gat gta<br>Phe Thr Asp Arg Ser Ser Val Pro Arg His Gln Phe Met Lys Asp Val<br>              320              325             330 | 131 |
| tgc ctg ttt ata cct gag cca ggc aac atg a aa gca agt ctt gca gtt | 179 |

```
                Cys Leu Phe Ile Pro Glu Pro Gly Asn Met Lys Ala Ser Leu Ala Val
                                335                 340                 345 tct gcg ata gca aga gca atg cat caa atg aac aag gtt gct ata gtg          227
Ser Ala Ile Ala Arg Ala Met His Gln Met Asn Lys Val Ala Ile Val
350                 355                 360 cga tgt gtg tgg agg caa ggt caa ggg aat gtt gct att ggt gta ttg          275
Arg Cys Val Trp Arg Gln Gly Gln Gly Asn Val Ala Ile Gly Val Leu
365                 370                 375                 380 acg cca aac att tca tca gtg aac aat atc caa gat tcc ttt tac ttc          323
Thr Pro Asn Ile Ser Ser Val Asn Asn Ile Gln Asp Ser Phe Tyr Phe
                385                 390                 395 aat gtg ctc cca ttt gct gag gac atc aga gag ttt cag ttt cgg tcc          371
Asn Val Leu Pro Phe Ala Glu Asp Ile Arg Glu Phe Gln Phe Arg Ser
                400                 405                 410 ttc agc agc ctg cca tca tca tct cag ccc act gaa gaa caa caa gaa          419
Phe Ser Ser Leu Pro Ser Ser Ser Gln Pro Thr Glu Glu Gln Gln Glu
                415                 420                 425 gct gca gat aac cta gtg aag atg tta gac cta gca cca cct gga aga          467
Ala Ala Asp Asn Leu Val Lys Met Leu Asp Leu Ala Pro Pro Gly Arg
        430                 435                 440 gag gtc ctc aag cct gag ttt acg cca aat ccc atc ttg gag aga ttt          515
Glu Val Leu Lys Pro Glu Phe Thr Pro Asn Pro Ile Leu Glu Arg Phe
445                 450                 455                 460 tac agt tac ctt gat ctc aag tca aag cag cca gat gca aat gtc cca          563
Tyr Ser Tyr Leu Asp Leu Lys Ser Lys Gln Pro Asp Ala Asn Val Pro
                465                 470                 475 ccg ctt gaa aga tct cta agg agg ata acc gaa cct gat cct gat gtg          611
Pro Leu Glu Arg Ser Leu Arg Arg Ile Thr Glu Pro Asp Pro Asp Val
                480                 485                 490 gtt ggc caa caa aca caa tta atc cag aat tta agc aaa gct ttt gtg          659
Val Gly Gln Gln Thr Gln Leu Ile Gln Asn Leu Ser Lys Ala Phe Val
        495                 500                 505 ctg aag gag aac ccc aag aaa aag aaa gca cga aca cag gac atg ttg          707
Leu Lys Glu Asn Pro Lys Lys Lys Lys Ala Arg Thr Gln Asp Met Leu
510                 515                 520 gca tat act ggt gca ggt gat caa gct aaa tct gta gag gac aga gtt          755
Ala Tyr Thr Gly Ala Gly Asp Gln Ala Lys Ser Val Glu Asp Arg Val
525                 530                 535                 540 ctg gaa aat aca cat cct tca aca gag agt gtt gtg gca atc aga gat          803
Leu Glu Asn Thr His Pro Ser Thr Glu Ser Val Val Ala Ile Arg Asp
                545                 550                 555 tca aat cca gtt caa gat ttt gag gcc atg ctg gct aag aga tct agc          851
Ser Asn Pro Val Gln Asp Phe Glu Ala Met Leu Ala Lys Arg Ser Ser
                560                 565                 570 tca aca tgg act cag aag gct att gga gat atg cag aat tac ata gca          899
Ser Thr Trp Thr Gln Lys Ala Ile Gly Asp Met Gln Asn Tyr Ile Ala
        575                 580                 585 gct ttg tta cag aac tcc agt gat ggg ggc aac tat caa aaa gca ctt          947
Ala Leu Leu Gln Asn Ser Ser Asp Gly Gly Asn Tyr Gln Lys Ala Leu
        590                 595                 600 gaa tgt ttt gct tct ctg cgg aag gcc tgt att att gaa cag gaa cca          995
Glu Cys Phe Ala Ser Leu Arg Lys Ala Cys Ile Ile Glu Gln Glu Pro
605                 610                 615                 620 cag gaa ttc aac cag ttc cta acg aac att tac gag aga ttg aag gaa          043
Gln Glu Phe Asn Gln Phe Leu Thr Asn Ile Tyr Glu Arg Leu Lys Glu
                625                 630                 635 ggt gat gct gcc aag ttc ttt caa ctt ctc tcc tca aaa aac att tca          091
Gly Asp Ala Ala Lys Phe Phe Gln Leu Leu Ser Ser Lys Asn Ile Ser
        640                 645                 650
```

-continued

```
ctt atc aac aaa gag gaa gcg cct gac agt g at gtg act gaa gag atg    139
Leu Ile Asn Lys Glu Glu Ala Pro Asp Ser A sp Val Thr Glu Glu Met
            655                 660                 665 gca aga agt ttc tac ctg aaa cga gaa aag g ta tct cag taggagctgg     188
Ala Arg Ser Phe Tyr Leu Lys Arg Glu Lys V al Ser Gln
        670                 675             680 aagaagccgg taactcgaag cgccttgggt ttggagatca tcggaggaat g gattgtgaa  248 actgggtatc tgtgtggggg catgttttga aactgggtat ctgggtggaa c tggaactaa 2308 tactcaaact ctctggggttg agtcactgtt ttgctgcaca atctgctgcc t actacgttt 2368 cgactagatt cagcttttaa aaaaaaaaaa aaaaaaaaaa aaaaaaaaa a            2419
```

<210> SEQ ID NO 2
<211> LENGTH: 681
<212> TYPE: PRT
<213> ORGANISM: Zea mays

<400> SEQUENCE: 2

```
Met Ala Arg Asn Arg Glu Val Val Ile Leu L eu Leu Asp Val Gly Pro
 1               5                  10                  15

Ser Met His Gly Val Leu Leu Glu Val Lys A sn Val Cys Leu Thr Leu
            20                  25                  30

Val His Lys Lys Leu Val Tyr Asn Arg Ser A sp Glu Val Gly Ile Val
        35                  40                  45

Leu Phe Gly Thr Lys Gly Thr Cys Asn Glu L eu Ala Lys Asp Ile Gly
    50                  55                  60

Gly Tyr Lys His Val Thr Val Ile His Asp I le Lys Val Val Asp Glu
65                  70                  75                  80

Gly Thr Ala Gln Ala Leu Gln Asn Leu Pro L eu Gly Ser Ala Pro Gly
                85                  90                  95

Asp Phe Leu Asp Ser Ile Val Val Gly Leu A sp Met Val Ile Arg Lys
            100                 105                 110

Phe Gly Ile Thr Lys Gly Lys Arg Arg Leu C ys Leu Ile Thr Ser Ala
        115                 120                 125

Gln Glu Leu Leu Arg Asp Pro Pro Glu Gly T hr Lys Glu Asp Gln Val
    130                 135                 140

Asp Thr Ile Ala Asp Met Leu Lys Lys His A sn Ile Lys Met Glu Cys
145                 150                 155                 160

Ile Ile Phe Arg Glu Pro Gly Val His His A sn Asp Ile Met Glu Glu
                165                 170                 175

Asn Asp Arg Leu Leu His Gln Phe Arg Asn A rg Ser Val Ala Lys Val
            180                 185                 190

Ile Gln Val Asp Asn Pro Thr Ser Leu Leu G ly Ala Leu Lys Thr Arg
        195                 200                 205

Asn Val Leu Pro Val Thr Val Phe Arg Gly A sp Leu Glu Val Asn Ser
    210                 215                 220

Asn Phe Lys Ile Lys Val Trp Val Tyr Lys L ys Thr Ala Glu Glu Lys
225                 230                 235                 240

Phe Pro Thr Leu Lys Lys Tyr Ser Asp Lys A la Pro Ser Asp Lys
                245                 250                 255

Phe Ala Ser His Glu Val Lys Val Asp Tyr G lu Tyr Lys Ser Val Val
            260                 265                 270

Glu Pro Asp Lys Val Val Pro Pro Asp Gln A rg Ile Lys Gly Tyr Leu
        275                 280                 285

Tyr Gly Pro Gln Val Ile Pro Val Ser Asn A la Glu Trp Glu Ala Val
```

-continued

```
                290                 295                 300
Lys Phe Lys Pro Glu Lys Gly Val Lys Leu L eu Gly Phe Thr Asp Arg
305                 310                 315                 320
Ser Ser Val Pro Arg His Gln Phe Met Lys A sp Val Cys Leu Phe Ile
                325                 330                 335
Pro Glu Pro Gly Asn Met Lys Ala Ser Leu A la Val Ser Ala Ile Ala
                340                 345                 350
Arg Ala Met His Gln Met Asn Lys Val Ala I le Val Arg Cys Val Trp
                355                 360                 365
Arg Gln Gly Gln Gly Asn Val Ala Ile Gly V al Leu Thr Pro Asn Ile
370                 375                 380
Ser Ser Val Asn Asn Ile Gln Asp Ser Phe T yr Phe Asn Val Leu Pro
385                 390                 395                 400
Phe Ala Glu Asp Ile Arg Glu Phe Gln Phe A rg Ser Phe Ser Ser Leu
                405                 410                 415
Pro Ser Ser Ser Gln Pro Thr Glu Glu Gln G ln Glu Ala Ala Asp Asn
                420                 425                 430
Leu Val Lys Met Leu Asp Leu Ala Pro Pro G ly Arg Glu Val Leu Lys
                435                 440                 445
Pro Glu Phe Thr Pro Asn Pro Ile Leu Glu A rg Phe Tyr Ser Tyr Leu
450                 455                 460
Asp Leu Lys Ser Lys Gln Pro Asp Ala Asn V al Pro Pro Leu Glu Arg
465                 470                 475                 480
Ser Leu Arg Arg Ile Thr Glu Pro Asp Pro A sp Val Val Gly Gln Gln
                485                 490                 495
Thr Gln Leu Ile Gln Asn Leu Ser Lys Ala P he Val Leu Lys Glu Asn
                500                 505                 510
Pro Lys Lys Lys Lys Ala Arg Thr Gln Asp M et Leu Ala Tyr Thr Gly
                515                 520                 525
Ala Gly Asp Gln Ala Lys Ser Val Glu Asp A rg Val Leu Glu Asn Thr
530                 535                 540
His Pro Ser Thr Glu Ser Val Val Ala Ile A rg Asp Ser Asn Pro Val
545                 550                 555                 560
Gln Asp Phe Glu Ala Met Leu Ala Lys Arg S er Ser Ser Thr Trp Thr
                565                 570                 575
Gln Lys Ala Ile Gly Asp Met Gln Asn Tyr I le Ala Ala Leu Leu Gln
                580                 585                 590
Asn Ser Ser Asp Gly Gly Asn Tyr Gln Lys A la Leu Glu Cys Phe Ala
                595                 600                 605
Ser Leu Arg Lys Ala Cys Ile Ile Glu Gln G lu Pro Gln Glu Phe Asn
                610                 615                 620
Gln Phe Leu Thr Asn Ile Tyr Glu Arg Leu L ys Glu Gly Asp Ala Ala
625                 630                 635                 640
Lys Phe Phe Gln Leu Leu Ser Ser Lys Asn I le Ser Leu Ile Asn Lys
                645                 650                 655
Glu Glu Ala Pro Asp Ser Asp Val Thr Glu G lu Met Ala Arg Ser Phe
                660                 665                 670
Tyr Leu Lys Arg Glu Lys Val Ser Gln
                675                 680
```

<210> SEQ ID NO 3
<211> LENGTH: 36
<212> TYPE: DNA
<213> ORGANISM: Artificial Sequence -continued

```
<220> FEATURE:
<223> OTHER INFORMATION: Designed oligonucleotide based upon an adaptor
      used for cDNA library construction and poly(dT) to remove clones
      which have a poly(A) tail but no cDNA insert.

<400> SEQUENCE: 3
tcgacccacg cgtccgaaaa aaaaaaaaaa aaaaaa                                36

<210> SEQ ID NO 4
<211> LENGTH: 732
<212> TYPE: PRT
<213> ORGANISM: Cricetulus griseus

<400> SEQUENCE: 4
```

| Met | Ala | Trp | Ser | Ala | Asn | Lys | Ala | Ala | Val | Val | Leu | Cys | Met | Asp | Val |
|---|---|---|---|---|---|---|---|---|---|---|---|---|---|---|---|
| 1 | | | | 5 | | | | | 10 | | | | | 15 | |

| Gly | Val | Ala | Met | Gly | Asn | Ser | Phe | Pro | Gly | Glu | Glu | Ser | Ser | Phe | Glu |
| | | | 20 | | | | | 25 | | | | | 30 | | |

| Gln | Ala | Lys | Lys | Val | Met | Thr | Met | Phe | Val | Gln | Arg | Gln | Val | Phe | Ser |
| | | | 35 | | | | | 40 | | | | 45 | | | |

| Glu | Ser | Lys | Asp | Glu | Ile | Ala | Leu | Val | Leu | Phe | Gly | Thr | Asp | Asn | Thr |
| | 50 | | | | | 55 | | | | | 60 | | | | |

| Asn | Asn | Ala | Leu | Ala | Ser | Glu | Asp | Gln | Tyr | Gln | Asn | Ile | Thr | Val | His |
| 65 | | | | | 70 | | | | | 75 | | | | | 80 |

| Arg | His | Leu | Met | Leu | Pro | Asp | Phe | Asp | Leu | Leu | Glu | Asp | Ile | Glu | Ser |
| | | | | 85 | | | | | 90 | | | | | 95 | |

| Lys | Ile | Gln | Leu | Gly | Ser | Arg | Gln | Ala | Asp | Ile | Leu | Asp | Ala | Leu | Ile |
| | | | | 100 | | | | | 105 | | | | | 110 | |

| Val | Cys | Met | Asp | Leu | Ile | Gln | Arg | Glu | Thr | Ile | Gly | Lys | Lys | Phe | Glu |
| | | | 115 | | | | | 120 | | | | | 125 | | |

| Lys | Lys | His | Ile | Glu | Val | Phe | Thr | Asp | Leu | Ser | Ser | Pro | Phe | Ser | Gln |
| | 130 | | | | | 135 | | | | | 140 | | | | |

| Asp | Gln | Leu | Asp | Val | Ile | Ile | Cys | Asn | Leu | Lys | Lys | Ser | Gly | Ile | Ser |
| 145 | | | | | 150 | | | | | 155 | | | | | 160 |

| Leu | Gln | Phe | Phe | Leu | Pro | Phe | Pro | Ile | Ser | Lys | Asn | Asp | Glu | Thr | Gly |
| | | | | 165 | | | | | 170 | | | | | 175 | |

| Asp | Arg | Gly | Asp | Gly | Asp | Leu | Gly | Leu | Asp | His | Cys | Gly | Pro | Ser | Phe |
| | | | 180 | | | | | 185 | | | | | 190 | | |

| Pro | Gln | Lys | Gly | Ile | Thr | Glu | Gln | Gln | Lys | Glu | Gly | Ile | Cys | Met | Val |
| | | | 195 | | | | | 200 | | | | | 205 | | |

| Glu | Arg | Val | Met | Val | Ser | Leu | Glu | Gly | Glu | Asp | Gly | Leu | Asp | Glu | Ile |
| | 210 | | | | | 215 | | | | | 220 | | | | |

| Tyr | Ser | Phe | Ser | Glu | Ser | Leu | Arg | Arg | Leu | Cys | Val | Phe | Lys | Lys | Ile |
| 225 | | | | | 230 | | | | | 235 | | | | | 240 |

| Glu | Arg | Arg | Ser | Met | Pro | Trp | Ser | Cys | Gln | Leu | Thr | Ile | Gly | Pro | Asp |
| | | | | 245 | | | | | 250 | | | | | 255 | |

| Leu | Ser | Ile | Lys | Ile | Val | Ala | Tyr | Lys | Ser | Ile | Val | Gln | Glu | Lys | Val |
| | | | 260 | | | | | 265 | | | | | 270 | | |

| Lys | Lys | Ser | Trp | Ile | Val | Val | Asp | Ala | Arg | Thr | Leu | Lys | Lys | Glu | Asp |
| | | | 275 | | | | | 280 | | | | | 285 | | |

| Ile | Arg | Lys | Glu | Thr | Val | Tyr | Cys | Leu | Asn | Asp | Asp | Asp | Glu | Thr | Glu |
| | 290 | | | | | 295 | | | | | 300 | | | | |

| Val | Ser | Lys | Glu | Asp | Thr | Ile | Gln | Gly | Phe | Arg | Tyr | Gly | Ser | Asp | Ile |
| 305 | | | | | 310 | | | | | 315 | | | | | 320 |

| Ile | Pro | Phe | Ser | Lys | Val | Asp | Glu | Glu | Gln | Met | Lys | Tyr | Lys | Ser | Glu |
| | | | | 325 | | | | | 330 | | | | | 335 | |

```
Gly Lys Cys Phe Ser Val Leu Gly Phe Cys A rg Ser Ser Gln Val His
            340                 345                 350

Arg Arg Phe Phe Met Gly Tyr Gln Val Leu L ys Val Phe Ala Ala Lys
        355                 360                 365

Asp Asp Glu Ala Ala Val Ala Leu Ser S er Leu Ile His Ala Leu
    370                 375                 380

Asp Glu Leu Asn Met Val Ala Ile Val Arg T yr Ala Tyr Asp Lys Arg
385                 390                 395                 400

Ala Asn Pro Gln Val Gly Val Ala Phe Pro T yr Ile Lys Asp Ser Tyr
                405                 410                 415

Glu Cys Leu Val Tyr Val Gln Leu Pro Phe M et Glu Asp Leu Arg Gln
            420                 425                 430

Tyr Met Phe Ser Ser Leu Lys Asn Asn Lys L ys Cys Thr Pro Thr Glu
        435                 440                 445

Ala Gln Leu Ser Ala Ile Asp Asp Leu Ile G lu Ser Met Ser Leu Val
    450                 455                 460

Lys Lys Ser Glu Glu Asp Thr Ile Glu A sp Leu Phe Pro Thr Ser
465                 470                 475                 480

Lys Ile Pro Asn Pro Glu Phe Gln Arg Phe P he Gln Cys Leu Leu His
                485                 490                 495

Arg Val Leu His Pro Gln Glu Arg Leu Pro P ro Ile Gln Gln His Ile
            500                 505                 510

Leu Asn Met Leu Asn Leu Pro Thr Glu Met L ys Ala Lys Cys Glu Ile
        515                 520                 525

Pro Leu Ser Lys Val Arg Thr Leu Phe Pro L eu Thr Glu Ala Val Lys
    530                 535                 540

Lys Lys Asp Gln Val Thr Ala Gln Asp Ile P he Gln Asp Ile His Glu
545                 550                 555                 560

Glu Gly Pro Ala Ala Lys Lys Cys Lys Thr G lu Lys Glu Glu Gly His
                565                 570                 575

Ile Ser Ile Ser Ser Val Ala Glu Gly Asn V al Thr Lys Val Gly Ser
            580                 585                 590

Val Asn Pro Val Glu Ser Phe Arg Val Leu V al Arg Gln Lys Ile Ala
        595                 600                 605

Ser Phe Glu Gln Ala Ser Leu Gln Leu Ile S er His Ile Glu Gln Phe
    610                 615                 620

Leu Asp Thr Asn Glu Thr Leu Tyr Phe Met L ys Ser Met Glu Cys Ile
625                 630                 635                 640

Lys Ala Phe Arg Glu Glu Ala Ile Gln Phe S er Glu Glu Arg Phe
                645                 650                 655

Asn Ser Phe Leu Glu Ala Leu Arg Glu Lys V al Glu Ile Lys Gln Leu
            660                 665                 670

Asn His Phe Trp Glu Ile Val Gln Asp G ly Val Thr Leu Ile Thr
        675                 680                 685

Lys Asp Glu Gly Ser Gly Ser Ser Val Thr T hr Glu Glu Ala Thr Lys
    690                 695                 700

Phe Leu Ala Pro Lys Asp Lys Ala Lys Glu A sp Ala Ala Gly Leu Glu
705                 710                 715                 720

Glu Gly Gly Asp Val Asp Asp Leu Leu Asp M et Ile
                725                 730

<210> SEQ ID NO 5
<211> LENGTH: 732
```

<212> TYPE: PRT
<213> ORGANISM: Mesocricetus auratus

<400> SEQUENCE: 5

```
Met Ala Trp Ser Ala Asn Lys Ala Ala Val Val Leu Cys Met Asp Val
1               5                   10                  15

Gly Ile Ala Met Gly Asn Ser Phe Pro Gly Glu Glu Ser Pro Phe Glu
            20                  25                  30

Gln Ala Lys Lys Val Met Thr Met Phe Val Gln Arg Gln Val Phe Ser
        35                  40                  45

Glu Ser Lys Asp Glu Ile Ala Leu Val Leu Phe Gly Thr Asp Ser Thr
    50                  55                  60

Glu Asn Ala Leu Ala Ser Glu Asp Gln Tyr Gln Asn Ile Thr Val Arg
65                  70                  75                  80

Arg His Leu Met Leu Pro Asp Phe Asp Leu Leu Glu Asp Ile Glu Ser
                85                  90                  95

Lys Ile Gln Leu Gly Ser Arg Gln Ala Asp Phe Leu Asp Ala Leu Ile
            100                 105                 110

Val Cys Met Asp Leu Ile Gln Arg Glu Thr Ile Gly Lys Lys Phe Gly
        115                 120                 125

Lys Lys His Ile Glu Val Phe Thr Asp Leu Ser Ser Pro Phe Ser Gln
    130                 135                 140

Asp Gln Leu Asp Val Ile Ile Cys Asn Leu Lys Lys Ser Gly Ile Ser
145                 150                 155                 160

Leu Gln Phe Phe Leu Pro Phe Pro Ile Ser Lys Asn Asn Glu Thr Gly
                165                 170                 175

His Ser Gly Asp Gly Asp Leu Gly Leu Asp His Arg Gly Pro Ser Phe
            180                 185                 190

Pro Gln Lys Gly Val Thr Glu Gln Gln Lys Glu Gly Ile Arg Met Val
        195                 200                 205

Glu Arg Val Met Val Ser Leu Glu Gly Glu Asp Gly Leu Asp Glu Ile
    210                 215                 220

Tyr Ser Phe Ser Glu Ser Leu Arg Gln Leu Cys Val Phe Lys Lys Ile
225                 230                 235                 240

Glu Arg Arg Ser Met Pro Trp Pro Cys Gln Leu Thr Ile Gly Pro Asp
                245                 250                 255

Leu Ser Ile Lys Ile Val Ala Tyr Lys Ser Ile Val Gln Glu Lys Leu
            260                 265                 270

Lys Lys Thr Trp Val Val Asp Ala Arg Thr Leu Lys Lys Glu Asp
        275                 280                 285

Ile Gln Lys Glu Thr Val Tyr Cys Leu Asn Asp Asp Glu Thr Glu
    290                 295                 300

Val Ser Lys Glu Asp Thr Ile Gln Gly Phe Arg Tyr Gly Ser Asp Ile
305                 310                 315                 320

Ile Pro Phe Ser Lys Val Asp Glu Glu Gln Met Lys Tyr Lys Ser Glu
                325                 330                 335

Gly Lys Cys Phe Ser Val Leu Gly Phe Cys Arg Ser Ser Gln Val His
            340                 345                 350

Arg Arg Phe Phe Met Gly Tyr Gln Val Leu Lys Val Phe Ala Ala Lys
        355                 360                 365

Asp Asp Glu Ala Ala Val Ala Leu Ser Ser Leu Ile His Ala Leu
    370                 375                 380

Asp Glu Leu Asn Met Val Ala Ile Val Arg Tyr Thr Tyr Asp Lys Arg
385                 390                 395                 400
```

```
Ala Asn Pro Gln Val Gly Val Ala Phe Pro Tyr Ile Lys Asp Ser Tyr
            405                 410                 415

Glu Cys Leu Val Tyr Val Gln Leu Pro Phe Met Glu Asp Leu Arg Gln
            420                 425                 430

Tyr Met Phe Ser Ser Leu Lys Asn Asn Lys Lys Cys Thr Pro Thr Glu
            435                 440                 445

Ala Gln Leu Ser Ala Ile Asp Asp Leu Ile Glu Ser Met Ser Leu Val
            450                 455                 460

Lys Lys Ser Glu Glu Asp Thr Ile Glu Asp Leu Phe Pro Thr Ser
465                 470                 475                 480

Lys Ile Pro Asn Pro Glu Phe Gln Arg Phe Phe Gln Cys Leu Leu His
            485                 490                 495

Arg Val Leu His Pro Gln Glu Arg Leu Pro Pro Ile Gln Gln His Ile
            500                 505                 510

Leu Asn Met Leu Asp Pro Pro Thr Glu Val Lys Ala Lys Cys Glu Ile
            515                 520                 525

Pro Leu Ser Lys Val Arg Thr Leu Phe Pro Leu Thr Glu Ala Val Lys
            530                 535                 540

Lys Lys Asp Gln Val Thr Ala Gln Asp Ile Phe Gln Asp Asn Asp Glu
545                 550                 555                 560

Glu Gly Pro Ala Ala Lys Lys Cys Lys Met Glu Lys Glu Ser His
            565                 570                 575

Ile Ser Ile Ser Ser Leu Ala Glu Gly Asn Val Thr Lys Val Gly Ser
            580                 585                 590

Val Asn Pro Val Glu Asn Phe Arg Val Leu Val Arg Gln Lys Ile Ala
            595                 600                 605

Ser Phe Glu Glu Ala Ser Leu Gln Leu Ile Ser His Ile Glu Gln Phe
            610                 615                 620

Leu Asp Thr Asn Glu Thr Leu Tyr Phe Met Lys Ser Met Glu Cys Ile
625                 630                 635                 640

Lys Ala Phe Arg Glu Glu Ala Ile Gln Phe Ser Glu Glu Gln Arg Phe
            645                 650                 655

Asn Ser Phe Leu Glu Ala Leu Arg Glu Lys Val Glu Ile Asn Glu Leu
            660                 665                 670

Asn His Phe Trp Glu Ile Val Val Gln Asp Gly Val Thr Leu Ile Thr
            675                 680                 685

Lys Asp Glu Gly Pro Gly Ser Ser Val Thr Thr Thr Glu Ala Thr Lys
            690                 695                 700

Phe Leu Ala Pro Lys Asp Lys Ala Lys Glu Asp Ser Ala Gly Leu Glu
705                 710                 715                 720

Glu Gly Gly Asp Val Asp Asp Leu Leu Asp Met Ile
            725                 730

<210> SEQ ID NO 6
<211> LENGTH: 732
<212> TYPE: PRT
<213> ORGANISM: Mus musculus

<400> SEQUENCE: 6

Met Ala Trp Ser Val Asn Lys Ala Ala Val Val Leu Cys Val Asp Val
  1               5                  10                  15

Gly Val Ala Met Gly Asn Ser Ile Pro Gly Glu Glu Ser Pro Ile Glu
             20                  25                  30

Gln Ala Lys Lys Val Met Thr Met Phe Val Gln Arg Gln Val Phe Ser
```

```
                  35                    40                     45
Glu Ser Lys Asp Glu Ile Ala Leu Ala Leu Tyr Gly Thr Asp Gly Thr
 50                      55                     60
Asp Met Pro Leu Ser Gly Lys Asp Gln Tyr Gln Asn Ile Thr Val Cys
 65                  70                     75                     80
Arg His Leu Met Leu Pro Asp Phe Asp Leu Leu Glu Asp Ile Gly Asn
                         85                     90                     95
Lys Ile Gln Pro Ser Gln Gln Ala Asp Phe Leu Asp Ala Leu Ile
                    100                    105                    110
Val Cys Met Asp Leu Ile Gln Arg Glu Thr Ile Gly Lys Lys Phe Gly
                    115                    120                    125
Lys Lys His Ile Glu Val Phe Thr Asp Leu Arg Ser Pro Phe Ser Lys
                    130                    135                    140
Asp Gln Leu Asp Val Ile Ile Cys Asn Leu Lys Lys Cys Gly Ile Ser
145                    150                    155                    160
Leu Gln Phe Phe Leu Pro Phe Pro Ile Asp Lys Asn Gly Glu Pro Gly
                         165                    170                    175
Glu Arg Gly Asp Leu Asp Ser Gly Leu Asp His Leu Lys Pro Ser Phe
                    180                    185                    190
Pro Gln Lys Gly Leu Thr Glu Gln Lys Glu Gly Ile Arg Met Val
                    195                    200                    205
Thr Arg Val Met Leu Ser Leu Glu Gly Glu Asp Gly Leu Asp Glu Ile
                    210                    215                    220
Tyr Ser Phe Ser Glu Ser Leu Arg Gln Leu Cys Val Phe Lys Lys Ile
225                    230                    235                    240
Glu Arg Arg Ser Met Pro Trp Pro Cys Gln Leu Thr Ile Gly Pro Asn
                         245                    250                    255
Leu Ser Ile Lys Ile Val Ala Tyr Lys Ser Ile Val Gln Glu Lys Phe
                    260                    265                    270
Lys Lys Ser Trp Val Val Asp Ala Arg Thr Leu Lys Lys Glu Asp
                    275                    280                    285
Ile Gln Lys Glu Thr Val Tyr Cys Leu Asn Asp Asp Glu Thr Glu
                    290                    295                    300
Val Ser Lys Glu Asp Thr Ile Gln Gly Tyr Arg Tyr Gly Ser Asp Ile
305                    310                    315                    320
Ile Pro Phe Ser Lys Val Asp Glu Glu Gln Met Lys Tyr Lys Ser Glu
                         325                    330                    335
Gly Lys Cys Phe Ser Val Leu Gly Phe Cys Lys Ser Ser Gln Val His
                    340                    345                    350
Arg Arg Phe Phe Met Gly His Gln Val Leu Lys Val Phe Ala Ala Lys
                    355                    360                    365
Asp Asp Glu Ala Ala Val Ala Leu Ser Ser Leu Val His Ala Leu
 370                    375                    380
Asp Glu Leu Asn Met Val Ala Ile Val Arg Tyr Ala Tyr Asp Lys Arg
385                    390                    395                    400
Ser Asn Pro Gln Val Gly Val Ala Ser Leu Tyr Ile Lys Asp Ala Tyr
                    405                    410                    415
Glu Arg Leu Val Tyr Val Gln Leu Pro Phe Met Glu Asp Leu Arg Gln
                    420                    425                    430
Tyr Met Phe Ser Ser Leu Lys Asn Asn Lys Lys Cys Thr Pro Thr Glu
                    435                    440                    445
Ala Gln Leu Ser Ala Ile Asp Asp Leu Ile Asp Ser Met Ser Leu Val
 450                    455                    460
```

Lys Lys Asn Glu Glu Asp Ile Val Glu Asp Leu Phe Pro Ala Ser
465                 470                 475                 480

Lys Ile Pro Asn Pro Glu Phe Gln Arg Leu Tyr Gln Cys Leu Leu His
            485                 490                 495

Arg Ala Leu His Leu Gln Glu Arg Leu Pro Pro Ile Gln Gln His Ile
                500                 505                 510

Leu Asn Ile Trp Asp Pro Pro Thr Glu Met Lys Gln Lys Cys Glu Ser
            515                 520                 525

Pro Pro Leu Lys Val Lys Thr Leu Phe Pro Leu Thr Glu Val Ile Lys
        530                 535                 540

Lys Lys Asn Gln Val Thr Ala Gln Asp Val Phe Gln Asp Asn His Glu
545                 550                 555                 560

Glu Gly Pro Ala Ala Lys Lys Tyr Lys Thr Glu Lys Glu Glu Asp His
                565                 570                 575

Ile Ser Ile Ser Ser Leu Ala Glu Gly Asn Ile Thr Lys Val Gly Ser
            580                 585                 590

Val Asn Pro Val Glu Asn Phe Arg Phe Leu Val Arg Gln Lys Ile Ala
        595                 600                 605

Ser Phe Glu Glu Ala Ser Leu Gln Leu Ile Ser His Ile Glu Gln Phe
610                 615                 620

Leu Asp Thr Asn Glu Thr Leu Tyr Phe Met Lys Ser Met Asp Cys Ile
625                 630                 635                 640

Lys Ala Phe Arg Glu Glu Ala Ile Gln Phe Ser Glu Glu Gln Arg Phe
                645                 650                 655

Asn Ser Phe Leu Glu Ala Leu Arg Glu Lys Val Glu Ile Lys Gln Leu
            660                 665                 670

Asn His Phe Trp Glu Ile Val Val Gln Asp Gly Val Thr Leu Ile Thr
        675                 680                 685

Lys Asp Glu Ala Pro Gly Ser Ser Ile Thr Ala Glu Ala Lys Lys
690                 695                 700

Phe Leu Ala Pro Lys Asp Lys Ala Lys Glu Asp Thr Thr Gly Pro Glu
705                 710                 715                 720

Glu Ala Gly Asp Val Asp Asp Leu Leu Asp Met Ile
                725                 730

<210> SEQ ID NO 7
<211> LENGTH: 731
<212> TYPE: PRT
<213> ORGANISM: Homo sapiens

<400> SEQUENCE: 7

Val Arg Ser Gly Asn Lys Ala Ala Val Leu Cys Met Asp Val Gly
1               5                   10                  15

Phe Thr Met Ser Asn Ser Ile Pro Gly Ile Glu Ser Pro Phe Glu Gln
            20                  25                  30

Ala Lys Lys Val Ile Thr Met Phe Val Gln Arg Gln Val Phe Ala Glu
        35                  40                  45

Asn Lys Asp Glu Ile Ala Leu Val Leu Phe Gly Thr Asp Gly Thr Asp
50                  55                  60

Asn Pro Leu Ser Gly Gly Asp Gln Tyr Gln Asn Ile Thr Val His Arg
65                  70                  75                  80

His Leu Met Leu Pro Asp Phe Asp Leu Leu Glu Asp Ile Glu Ser Lys
                85                  90                  95

Ile Gln Pro Gly Ser Gln Gln Ala Asp Phe Leu Asp Ala Leu Ile Val

-continued

```
                100                   105                   110
Ser Met Asp Val Ile Gln His Glu Thr Ile Gly Lys Lys Phe Glu Lys
            115                   120                   125
Arg His Ile Glu Ile Phe Thr Asp Leu Ser Ser Arg Phe Ser Lys Ser
130                   135                   140
Gln Leu Asp Ile Ile Ile His Ser Leu Lys Lys Cys Asp Ile Ser Leu
145                   150                   155                   160
Gln Phe Phe Leu Pro Phe Ser Leu Gly Lys Glu Asp Gly Ser Gly Asp
                165                   170                   175
Arg Gly Asp Gly Pro Phe Arg Leu Gly Gly His Gly Pro Ser Phe Pro
                180                   185                   190
Leu Lys Gly Ile Thr Glu Gln Gln Lys Glu Gly Leu Glu Ile Val Lys
                195                   200                   205
Met Val Met Ile Ser Leu Glu Gly Asp Gly Leu Asp Glu Ile Tyr
            210                   215                   220
Ser Phe Ser Glu Ser Leu Arg Lys Leu Cys Val Phe Lys Lys Ile Glu
225                   230                   235                   240
Arg His Ser Ile His Trp Pro Cys Arg Leu Thr Ile Gly Ser Asn Leu
                245                   250                   255
Ser Ile Arg Ile Ala Ala Tyr Lys Ser Ile Leu Gln Glu Arg Val Lys
                260                   265                   270
Lys Thr Trp Thr Val Val Asp Ala Lys Thr Leu Lys Lys Glu Asp Ile
            275                   280                   285
Gln Lys Glu Thr Val Tyr Cys Leu Asn Asp Asp Asp Glu Thr Glu Val
            290                   295                   300
Leu Lys Glu Asp Ile Ile Gln Gly Phe Arg Tyr Gly Ser Asp Ile Val
305                   310                   315                   320
Pro Phe Ser Lys Val Asp Glu Glu Gln Met Lys Tyr Lys Ser Glu Gly
                325                   330                   335
Lys Cys Phe Ser Val Leu Gly Phe Cys Lys Ser Ser Gln Val Gln Arg
                340                   345                   350
Arg Phe Phe Met Gly Asn Gln Val Leu Lys Val Phe Ala Ala Arg Asp
                355                   360                   365
Asp Glu Ala Ala Val Ala Leu Ser Ser Leu Ile His Ala Leu Asp
            370                   375                   380
Asp Leu Asp Met Val Ala Ile Val Arg Tyr Ala Tyr Asp Lys Arg Ala
385                   390                   395                   400
Asn Pro Gln Val Gly Val Ala Phe Pro His Ile Lys His Asn Tyr Glu
                405                   410                   415
Cys Leu Val Tyr Val Gln Leu Pro Phe Met Glu Asp Leu Arg Gln Tyr
                420                   425                   430
Met Phe Ser Ser Leu Lys Asn Ser Lys Lys Tyr Ala Pro Thr Glu Ala
            435                   440                   445
Gln Leu Asn Ala Val Asp Ala Leu Ile Asp Ser Met Ser Leu Ala Lys
            450                   455                   460
Lys Asp Glu Lys Thr Asp Thr Leu Glu Asp Leu Phe Pro Thr Thr Lys
465                   470                   475                   480
Ile Pro Asn Pro Arg Phe Gln Arg Leu Phe Gln Cys Leu Leu His Arg
                485                   490                   495
Ala Leu His Pro Arg Glu Pro Leu Pro Pro Ile Gln Gln His Ile Trp
                500                   505                   510
Asn Met Leu Asn Pro Pro Ala Glu Val Thr Thr Lys Ser Gln Ile Pro
            515                   520                   525
```

-continued

```
Leu Ser Lys Ile Lys Thr Leu Phe Pro Leu Ile Glu Ala Lys Lys Lys
    530                 535                 540

Asp Gln Val Thr Ala Gln Glu Ile Phe Gln Asp Asn His Glu Asp Gly
545                 550                 555                 560

Pro Thr Ala Lys Lys Leu Lys Thr Glu Gln Gly Gly Ala His Phe Ser
            565                 570                 575

Val Ser Ser Leu Ala Glu Gly Ser Val Thr Ser Val Gly Ser Val Asn
            580                 585                 590

Pro Ala Glu Asn Phe Arg Val Leu Val Lys Gln Lys Lys Ala Ser Phe
        595                 600                 605

Glu Glu Ala Ser Asn Gln Leu Ile Asn His Ile Glu Gln Phe Leu Asp
    610                 615                 620

Thr Asn Glu Thr Pro Tyr Phe Met Lys Ser Ile Asp Cys Ile Arg Ala
625                 630                 635                 640

Phe Arg Glu Glu Ala Ile Lys Phe Ser Glu Glu Gln Arg Phe Asn Asn
            645                 650                 655

Phe Leu Lys Ala Leu Gln Glu Lys Val Glu Ile Lys Gln Leu Asn His
            660                 665                 670

Phe Trp Glu Ile Val Val Gln Asp Gly Ile Thr Leu Ile Thr Lys Glu
        675                 680                 685

Glu Ala Ser Gly Ser Ser Val Thr Ala Glu Glu Ala Lys Lys Phe Leu
    690                 695                 700

Ala Pro Lys Asp Lys Pro Ser Gly Asp Thr Ala Ala Val Phe Glu Glu
705                 710                 715                 720

Gly Gly Asp Val Asp Asp Leu Leu Asp Met Ile
                725                 730
```

KU80 HOMOLOGUE AND USES THEREOF

CROSS-REFERENCE TO RELATED APPLICATIONS

This application claims the benefit of U.S. application Ser. No. 60/126,214 filed Mar. 25, 1999, which is herein incorporated by reference.

TECHNICAL FIELD

The present invention relates generally to plant molecular biology. More specifically, it relates to nucleic acids and methods for modulating their expression in plants.

BACKGROUND OF THE INVENTION

Cellular DNA undergoes double strand breakage during the course of many physiological events as well as in response to a variety of environmental insults (Friedburg, E., Walker, G. and Siede, W., *DNA Repair and Mutagenesis*, ASM Press, Washington D.C., 1995; Nickollof J. and Hoekstra, M., *DNA Damage and Repair*, Humana Press, Totowa, N.J., 1998). Left un-repaired, such double strand breaks (DSBs) lead to mutations that may prove lethal to the organism. Therefore, these DSBs are repaired promptly via two independent pathways: i) homologous recombination ii) non-homologous end joining (Friedburg, E., Walker, G. and Siede, W., *DNA Repair and Mutagenesis*, ASM Press, Washington D.C., 1995; Nickollof J. and Hoekstra, M., *DNA Damnage and Repair*, Humana Press, Totowa, N.J., 1998). The first pathway involves a series of very specific biochemical reactions catalyzed by a complex of cellular proteins (Shinohara and Ogawa, *Trends in Biochem. Sci.* 237: 387–391, 1995). Due to the large number of proteins involved in this complex, it is referred to as a 'recombinosome' (Hays et al., *Proc. Natl. Acad. Sci. USA* 92: 6925–6929, 1995). This pathway is the dominant mode of DSB repair in lower eukaryotes such as yeast (Nickollof J. and Hoekstra, M., *DNA Damage and Repair*, Humana Press, Totowa, N.J., 1998)

The non-homologous end-joining pathway is the major route of DSB repair in higher eukaryotes (Friedburg, E., Walker, G. and Siede, W., *DNA Repair and Mutagenesis*, ASM Press, Washington DC., 1995; Nickollof J. and Hoekstra, M., *DNA Damage and Repair*, Humana Press, Totowa, N.J., 1998). This pathway is also catalyzed by a group of cellular proteins. This group contains, in addition to hitherto unidentified factors, some well-characterized enzymes such as DNA ligases, Poly(ADP-Ribose) Polymerase [PADPRP], and DNA -dependent Protein Kinase [DNA-PK] (Lindahl et al., *Trends in Biochem. Sci.* 237: 405–411, 1995; Jackson & Jeggo, *Trends in Biochem. Sci.* 237: 412–415, 1995). These enzymes have been studied in detail using lower as well as higher vertebrate systems including mammals. Both PADPRP and DNA-PK have been shown to be activated by DNA ends. Moreover, these two enzymes also bind DNA ends (Lindahl et al., *Trends in Biochem. Sci.* 237: 405–411, 1995; Jackson & Jeggo, *Trends in Biochem. Sci.* 237: 412–415, 1995). While PADPRP is a single polypeptide of ~115 kDa, DNA-PK exists as a complex of two subunits (Shah et al., *Anal. Biochem.* 227: 1–13, 1995; Dvir et al., *Proc. Natl. Acad. Sci. USA* 89: 11920–11924, 1992; Anderson et al., *Crit. Rev. Eukaryot. Gene Express.* 4: 283–314, 1992). The catalytic subunit [DNA-PK$_{cs}$] is composed of a single polypeptide of ~450 kDa. It is a serine-threonine type of protein kinase that phosphorylates a variety of nuclear enzymes, transcription factors and oncogenes (Anderson et al., *Crit. Rev. Eukaryot. Gene Express.* 4: 283–314, 1992). However, DNA-PK$_{cs}$ by itself does not bind DNA. The non-catalytic subunit of DNA-PK is a heterodimer composed of 70 kDa and 86 kDa proteins. The non-catalytic subunit acts as a regulator of DNA-PK$_{cs}$ by virtue of its' ability to bind to DNA ends, thereby recruiting the catalytic subunit to the site of DSBs (Dvir et al., *Proc. Natl. Acad. Sci. USA* 89: 11920–11924, 1992; Anderson et al., *Crit. Rev. Eukaryot. Gene Express.* 4: 283–314, 1992).

Although the enzymology of DNA-PK$_{cs}$ has been investigated extensively, its biological function was identified only recently (Dvir et al., *Proc. Natl. Acad. Sci. USA* 89: 11920–11924, 1992 ;Jeggo, *Mutation Res.* 384: 1–14, 1997). Availability of the full-length cDNA sequence of mammalian DNA-PK$_{cs}$ allowed identification of this protein as a member of the phosphotidyl inositol 3-kinase (PI kinase) gene family. While most members of this family are lipid kinases, a small number of proteins forming a subfamily specifically phosphorylate proteins. Members of this subfamily are known as PI-K related kinases and include the ATM protein, Tel1p, Tor1p, Tor2p, FRAP, Rad3p, Mec1p and Mei41 (Jeggo, *Mutation Res.* 384: 1–14, 1997). In addition to their structural and biochemical similarities, members of this subfamily also appear to share a common biological function. They are all involved in repair of DNA that is damaged in response to a variety of genetic, physiological or environmental events (Jeggo, *Mutation Res.* 384: 1–14, 1997). Although several members of this subfamily have been cloned from animals, no information on plant DNA-PK$_{cs}$ is available in the literature.

The non-catalytic subunit of DNA-PK consists of two proteins of ~70 kDa and 86 kDa (Dvir et al., *Proc. Natl. Acad. Sci. USA* 89: 11920–11924, 1992; Gotlib and Jackson, *Cell* 72: 131–142, 1993). These two proteins appear to be identical to previously well-characterized mammalian Ku proteins (Dvir et al., *Proc. Natl. Acad. Sci. USA* 89: 11920–11924, 1992). The Ku complex, also a heterodimer of 70 kDa and 86 kDa proteins, was shown to be a nuclear DNA-binding autoantigen (Mimori et al., *J. Clin. Invest.* 68: 611–620, 1981; Mimori et al., *J. Biol. Chem.* 261: 2274–2278, 1986). Patients diagnosed with a variety of autoimmune diseases have been known to develop antibodies to Ku proteins (Yaneva & Arnettt, *Clin. Exp. Immunol.* 76: 366–372, 1989). Further biochemical analysis has established that Ku binds with strong affinity to DNA ends, stem-loop structures, DNA bubbles, or transitions between double stranded DNA and two single strands (Chu, *J. Biol. Chem.* 272: 24097–24100, 1997). Subsequent to binding to the ends, Ku molecules can translocate along the DNA, such that three or more molecules can bind to the linear DNA fragment. Both components of Ku have a DNA dependent ATPase activity and an ATP dependent helicase activity (Chu, *J. Biol. Chem.* 272: 24097–24100, 1997). Recently, Yoo and Dynan have also demonstrated RNA binding activity of the Ku protein (Yoo & Dynan, *Biochemistry* 37: 1336–1343, 1998).

Recent genetic studies using rodent cell lines defective in DNA strand break repair have provided the important link between Ku protein, DNA-PK and DSB repairs during DNA replication, repair and recombination (Yoo & Dynan, *Biochemistry* 37: 1336–1343, 1998). Boulton & Jackson have shown that the yeast Ku70 potentiates illegitimate DNA DSB repair and serves as a barrier to error-prone DNA repair pathways (Boulton & Jackson, *EMBO J.* 15: 5093–5103, 1996). Studies with mutant rodent cell lines have clearly shown that Ku proteins are required for the V (D) J DNA recombination and immunoglobulin isotype switching (Roth et al., *Current Biol.* 5: 496–498, 1995; Casellas et al., *EMBO J.* 17: 2404–2411, 1998). Components of DNA-PK are also involved in the non-homologous end-joining pathway in telomeric length maintenance and telomere silencing as well as telomere integrity (Boulton & Jackson, *EMBO J.* 17: 1819–1828, 1998; Polotnianka et al., *Current Biol.* 8: 831–834, 1998). Ramsden & Gellert have recently observed that Ku protein stimulates DNA end joining by mammalian DNA ligases and proposed a direct role for Ku in DSB repair (Ramsden & Gellert, *EMBO J.* 17: 609–614, 1998). A role for Ku protein in modulation of heat shock response and hyperthermic radiosensitization has also been advocated (Yang et al., *Mol. Cell. Biol.* 16: 3799–3806, 1996; Burgman et al., *Cancer Res.* 57: 2847–2850, 1997). As discussed above, recent studies have established the role of DNA-PK components in various cellular processes involving DSB. During the course of these investigations, Ku homologues have been cloned from human, mouse, Drosophila melanogaster, Rhipicephalus appendiculatus and Caenorhabditis elegans (Reeves & Sthoeger, *J. Biol. Chem.* 264: 5047–5052, 1989; Chan et al., *J. Biol. Chem.* 264: 3651–3654, 1989; Porges et al., *J. Immunol.* 145: 4222–4228, 1990; Jacoby et al., *J. Biol. Chem.* 269: 11484–11491, 1994; Paesen et al., *Biochim Biophys. Acta* 1305: 120–124, 1996; Boulton & Jackson, *Nucleic Acid Res.* 24: 4639–4648, 1996). Interestingly, Ku homologues have also been reported in Saccharomyces cerevisiae (Feldmann & Winnacker, *J. Biol. Chem.* 268: 12895–12900, 1993; Feldmann et al., *J. Biol. Chem.* 271: 27765–27769, 1996; Boulton & Jackson, *Nucleic Acid Res.* 24: 4639–4648, 1996; Wang et al, *J. Biol. Chem.* 273: 842–848, 1998). However, despite wide speculations and exhaustive research by many individuals, the presence of DNA-PK components in plants has never been documented.

Control of homologous recombination or non-homologous end joining by modulating Ku provides the means to modulate the efficiency which heterologous nucleic acids are incorporated into the genomes of a target plant cell. Control of these processes has important implications in the creation of novel recombinantly engineered crops such as maize. The maize Ku80 orthologue of the present invention provides this and other advantages.

SUMMARY OF THE INVENTION

Generally, it is the object of the present invention to provide nucleic acids and proteins relating to the maize Ku80 homolog. It is an object of the present invention to provide: 1) antigenic fragments of the proteins of the present invention; 2) transgenic plants comprising the nucleic acids of the present invention; 3) methods for modulating, in a transgenic plant, the expression of the nucleic acids of the present invention.

Therefore, in one aspect, the present invention relates to an isolated nucleic acid comprising a member selected from the group consisting of (a) a polynucleotide having a specified sequence identity to a polynucleotide encoding a polypeptide of the present invention; (b) a polynucleotide which is complementary to the polynucleotide of (a); and, (c) a polynucleotide comprising a specified number of contiguous nucleotides from a polynucleotide of (a) or (b). The isolated nucleic acid can be DNA.

In another aspect, the present invention relates to recombinant expression cassettes, comprising a nucleic acid of the present invention operably linked to a promoter.

In another aspect, the present invention is directed to a host cell into which has been introduced the recombinant expression cassette.

In a further aspect, the present invention relates to an isolated protein comprising a polypeptide having a specified number of contiguous amino acids encoded by an isolated nucleic acid of the present invention.

In another aspect, the present invention relates to an isolated nucleic acid comprising a polynucleotide of specified length which selectively hybridizes under stringent conditions to a polynucleotide of the present invention, or a complement thereof. In some embodiments, the isolated nucleic acid is operably linked to a promoter.

In another aspect, the present invention relates to a recombinant expression cassette comprising a nucleic acid amplified from a library as referred to supra, wherein the nucleic acid is operably linked to a promoter. In some embodiments, the present invention relates to a host cell transfected with this recombinant expression cassette. In some embodiments, the present invention relates to a protein of the present invention that is produced from this host cell.

In yet another aspect, the present invention relates to a transgenic plant comprising a recombinant expression cassette comprising a plant promoter operably linked to any of the isolated nucleic acids of the present invention. The present invention also provides transgenic seed from the transgenic plant.

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5$^{th}$ edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The term "antibody" includes reference to antigen binding forms of antibodies (e.g., Fab, F(ab)$_2$). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "antigen" includes reference to a substance to which an antibody can be generated and/or to which the antibody is specifically immunoreactive. The specific immunoreactive sites within the antigen are known as epitopes or antigenic determinants. These epitopes can be a linear array of monomers in a polymeric composition—such as amino acids in a protein - or consist of or comprise a more complex secondary or tertiary structure. Those of skill will recognize that all immunogens (i.e., substances capable of eliciting an immune response) are antigens; however some antigens, such as haptens, are not immunogens but may be made immunogenic by coupling to a carrier molecule. An antibody immunologically reactive with a particular antigen can be generated in vivo or by recombinant methods such as selection of libraries of recombinant antibodies in phage or similar vectors. See, e.g., Huse et al., *Science* 246: 1275–1281 (1989); and Ward, et al., *Nature* 341: 544–546 (1989); and Vaughan et al., *Nature Biotech.* 14: 309–314 (1996).

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

As used herein, "chromosomal region" includes reference to a length of a chromosome that may be measured by reference to the linear segment of DNA that it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). See also, Creighton (1984) Proteins W.H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17: 477–498 (1989)). Thus, the maize preferred codon for a particular amino acid may be derived from known gene sequences from maize. Maize codon usage for 28 genes from maize plants are listed in Table 4 of Murray et al., supra.

As used herein "full-length sequence" in reference to a specified polynucleotide or its encoded protein means having the entire amino acid sequence of, a native (non-synthetic), endogenous, biologically active form of the specified protein. Methods to determine whether a sequence is full-length are well known in the art including such exemplary techniques as northern or western blots, primer extension, S1 protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN AUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as E. coli, or eukaryotic cells such as yeast, insect, amphibian, or mammalian cells. Preferably, host cells are monocotyledonous or dicotyledonous plant cells. A particularly preferred monocotyledonous host cell is a maize host cell.

A The term "hybridization complex" includes reference to a duplex nucleic acid structure formed by two single-stranded nucleic acid sequences selectively hybridized with each other.

By "immunologically reactive conditions" or "immunoreactive conditions" is meant conditions which allow an antibody, reactive to a particular epitope, to bind to that epitope to a detectably greater degree (e.g., at least 2-fold over background) than the antibody binds to substantially any other epitopes in a reaction mixture comprising the particular epitope. Immunologically reactive conditions are dependent upon the format of the antibody binding reaction and typically are those utilized in immunoassay protocols. See Harlow and Lane, *Antibodies, A Laboratory Manual*, Cold Spring Harbor Publications, New York (1988), for a description of immunoassay formats and conditions.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

Unless otherwise stated, the term "maize Ku80 nucleic acid" is a nucleic acid of the present invention and means a nucleic acid comprising a polynucleotide of the present invention (a "maize Ku80 polynucleotide") encoding a maize Ku80 polypeptide. A "maize Ku80 gene" is a gene of the present invention and refers to a heterologous genomic form of a full-length maize Ku80 polynucleotide.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2nd ed., Vol. 1–3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants. A particularly preferred plant is *Zea mays*.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylationof glutamic acid residues, hydroxylation and ADP-ribosylation. It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether nor not its origin is a plant cell. Exemplary plant promoters include, but are not limited to, those that are obtained from plants, plant viruses, and bacteria which comprise genes expressed in plant cells such Agrobacterium or Rhizobium. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

The term "maize Ku80 polypeptide" is a polypeptide of the present invention and refers to one or more amino acid sequences, in glycosylated or non-glycosylated form. The term is also inclusive of fragments, variants, homologs, alleles or precursors (e.g., preproproteins or proproteins) thereof. A "maize Ku80 protein" is a protein of the present invention and comprises a maize Ku80 polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "specifically reactive", includes reference to a binding reaction between an antibody and a protein having an epitope recognized by the antigen binding site of the antibody. This binding reaction is determinative of the presence of a protein having the recognized epitope amongst the presence of a heterogeneous population of proteins and other biologics. Thus, under designated immunoassay conditions, the specified antibodies bind to an analyte having the recognized epitope to a substantially greater degree (e.g., at least 2-fold over background) than to substantially all analytes lacking the epitope which are present in the sample.

Specific binding to an antibody under such conditions may require an antibody that is selected for its specificity for a particular protein. For example, antibodies raised to the polypeptides of the present invention can be selected from to obtain antibodies specifically reactive with polypeptides of the present invention. The proteins used as immunogens can be in native conformation or denatured so as to provide a linear epitope.

A variety of immunoassay formats may be used to select antibodies specifically reactive with a particular protein (or other analyte). For example, solid-phase ELISA immunoassays are routinely used to select monoclonal antibodies specifically immunoreactive with a protein. See Harlow and Lane, *Antibodies, A Laboratory Manual*, Cold Spring Harbor Publications, New York (1988), for a description of immunoassay formats and conditions that can be used to determine selective reactivity.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267–284 (1984): $T_m$=81.5° C.+16.6 (log M)+0.41 (%GC)–0.61 (% form)–500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant reeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps)

compared to the reference sequence (which does not comprise additions or deletions) for optimal alignment of the two sequences. Generally, the comparison window is at least 20 contiguous nucleotides/amino acids residues in length, and optionally can be 30, 40, 50, 100, or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2: 482 (1981); by the homology alignment algorithm of Needleman and Wunsch, *J. Mol. Biol.* 48: 443 (1970); by the search for similarity method of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, California; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237–244 (1988); Higgins and Sharp, *CABIOS* 5: 151–153 (1989); Corpet, et al., *Nucleic Acids Research* 16: 10881–90 (1988); Huang, et al., *Computer Applications in the Biosciences* 8: 155–65 (1992), and Pearson, et al., *Methods in Molecular Biology* 24: 307–331 (1994).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Software for performing BLAST analyses is publicly available, e.g., through the National Center for Biotechnology Information. This algorithm involves first identifying high scoring sequence pairs (HSPs) by identifying short words of length W in the query sequence which either match or satisfy some positive-valued threshold score T when aligned with a word of the same length in a database sequence. T is referred to as the neighborhood word score threshold These initial neighborhood word hits act as seeds for initiating searches to find longer HSPs containing them The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W. T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5877 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149–163 (1993)) and XNU (Claverie and States, *Comput. Chem.*, 17:191–201 (1993)) low-complexity filters can be employed alone or in combination.

GAP can also be used to compare a polynucleotide or polypeptide of the present invention with a reference sequence. GAP uses the algorithm of Needleman and Wunsch (*J. Mol. Biol.* 48: 443–453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can each independently be: 0, 1, 2, 3, 4, 5, 6, 7, 8, 9, 10, 15, 20, 30, 40, 50, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) *Proc. Natl. Acad. Sci. USA* 89:10915).

Unless otherwise stated, sequence identity/similarity values provided herein refer to the value obtained using the BLAST 2.0 suite of programs using default parameters (Altschul et al., *Nucleic Acids Res.* 25:3389–3402, 1997; Altschul et al., J. Mol. Bio. 215: 403–410, 1990) or to the value obtained using the GAP program using default parameters (see the Wisconsin Genetics Software Package, Genetics Computer Group (GCG), 575 Science Dr., Madison, Wis., USA).

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the finctional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, hereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4: 11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) (ii) The terms "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Optionally, optimal alignment is conducted using the homology alignment algorithm of Needleman and Wunsch, *J. Mol. Biol.* 48: 443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

DETAILED DESCRIPTION OF THE INVENTION

Overview

The present invention provides, among other things, compositions and methods for modulating (i.e., increasing or decreasing) the level of polynucleotides and polypeptides of the present invention in plants. In particular, the polynucleotides and polypeptides of the present invention can be expressed temporally or spatially, e.g., at developmental stages, in tissues, and/or in quantities, which are uncharacteristic of non-recombinantly engineered plants. Thus, the present invention provides utility in such exemplary applications as in the control of homologous recombination efficiency or transformation efficiency in plants.

The present invention also provides isolated nucleic acid comprising polynucleotides of sufficient length and complementarity to a gene of the present invention to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms), orthologs, or paralogs of the gene, or for site directed mutagenesis in eukaryotic cells (see, e.g., U.S. Pat. No. 5,565,350). The isolated nucleic acids of the present invention can also be used for recombinant expression of their encoded polypeptides, or for use as immunogens in the preparation and/or screening of antibodies. The isolated nucleic acids of the present invention can also be employed for use in sense or antisense suppression of one or more genes of the present invention in a host cell, tissue, or plant. Attachment of chemical agents which bind, intercalate, cleave and/or crosslink to the isolated nucleic acids of the present invention can also be used to modulate transcription or translation.

The present invention also provides isolated proteins comprising a polypeptide of the present invention (e.g., preproenzyme, proenzyme, or enzymes). The present invention also provides proteins comprising at least one epitope from a polypeptide of the present invention. The proteins of the present invention can be employed in assays for enzyme agonists or antagonists of enzyme function, or for use as immunogens or antigens to obtain antibodies specifically immunoreactive with a protein of the present invention. Such antibodies can be used in assays for expression levels, for identifying and/or isolating nucleic acids of the present invention from expression libraries, for identification of homologous polypeptides from other species, or for purification of polypeptides of the present invention.

The isolated nucleic acids and polypeptides of the present invention can be used over a broad range of plant types, particularly monocots such as the species of the family Gramineae including Hordeum, Secale, Triticum, Sorghum (e.g., *S. bicolor*) and Zea (e.g., *Z. mays*). The isolated nucleic acid and proteins of the present invention can also be used in species from the genera: Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, and Avena.

Nucleic Acids

The present invention provides, among other things, isolated nucleic acids of RNA, DNA, and analogs and/or chimeras thereof, comprising a polynucleotide of the present invention.

A polynucleotide of the present invention is inclusive of:
(a) a polynucleotide encoding a polypeptide of SEQ ID NO: 2 and conservatively modified and polymorphic variants thereof, including exemplary polynucleotides of SEQ ID NO: 1; nucleotide sequences of the invention also include the maize Ku80 sequence as contained in a plasmid deposited in a bacterial host with American Type Culture Collection (ATCC) and assigned Accession Number 207148.
(b) a polynucleotide which is the product of amplification from a Zea mays nucleic acid library using primer pairs which selectively hybridize under stringent conditions to loci within a polynucleotide selected from the group consisting of SEQ ID NO: 1, or the sequence as contained in ATCC deposit assigned Accession No. 207148, wherein the polynucleotide has substantial sequence identity to a polynucleotide selected from the group consisting of SEQ ID NO: 1; or the sequence as contained in ATCC deposit assigned Accession No. 207148.
(c) a polynucleotide which selectively hybridizes to a polynucleotide of (a) or (b);
(d) a polynucleotide having a specified sequence identity with polynucleotides of (a), (b), or (c);
(e) a polynucleotide encoding a protein having a specified number of contiguous amino acids from a prototype polypeptide, wherein the protein is specifically recognized by antisera elicited by presentation of the protein and wherein the protein does not detectably immunoreact to antisera which has been fully immunosorbed with the protein;
(f) complementary sequences of polynucleotides of (a), (b), (c), (d), or (e); and
(g) a polynucleotide comprising at least a specific number of contiguous nucleotides from a polynucleotide of (a), (b), (c), (d), (e), or (f).

The polynucleotide of SEQ ID NO: 1 is contained in a plasmid deposited with American Type Culture Collection (ATCC) on Mar. 3, 1999 and assigned Accession Number 207148. American Type Culture Collection is located at 10801 University Blvd., Manassas, Va. 20110–2209.

The ATCC deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. Section 112.

A. Polynucleotides Encoding A Polypeptide of the Present Invention or Conservatively Modified or Polymorphic Variants Thereof As indicated in (a), above, the present invention provides isolated nucleic acids comprising a polynucleotide of the present invention, wherein the polynucleotide encodes a polypeptide of the present invention, or conservatively modified or polymorphic variants thereof. Accordingly, the present invention includes polynucleotides of SEQ ID NO: 1, and the sequence as contained in ATCC deposit assigned Accession No. 207148 and silent variations of polynucleotides encoding a polypeptide of SEQ ID NO: 2. The present invention further provides isolated nucleic acids comprising polynucleotides encoding conservatively modified variants of a polypeptide of SEQ ID NO: 2. Conservatively modified variants can be used to generate or select antibodies immunoreactive to the non-variant polypeptide. Additionally, the present invention further provides isolated nucleic acids comprising polynucleotides encoding one or more allelic (polymorphic) variants of polypeptides/polynucleotides. Polymorphic variants are frequently used to follow segregation of chromosomal regions in, for example, marker assisted selection methods for crop improvement.

B. Polynucleotides Amplifiedfrom a *Zea mays* Nucleic Acid Library

As indicated in (b), above, the present invention provides an isolated nucleic acid comprising a polynucleotide of the present invention, wherein the polynucleotides are amplified from a *Zea mays* nucleic acid library. *Zea mays* lines B73, PHRE1, A632, BMS-P2#10, W23, and Mo17 are known and publicly available. Other publicly known and available maize lines can be obtained from the Maize Genetics Cooperation (Urbana, Ill.). The nucleic acid library may be a cDNA library, a genomic library, or a library generally constructed from nuclear transcripts at any stage of intron processing. cDNA libraries can be normalized to increase the representation of relatively rare cDNAs. In optional embodiments, the cDNA library is constructed using a full-length cDNA synthesis method. Examples of such methods include Oligo-Capping (Maruyama, K. and Sugano, S. *Gene* 138: 171–174, 1994), Biotinylated CAP Trapper (Carninci, P., Kvan, C., et al. *Genomics* 37: 327–336, 1996), and CAP Retention Procedure (Edery, E., Chu, L. L., et al. *Molecular and Cellular Biology* 15: 3363–3371, 1995). cDNA synthesis is often catalyzed at 50–55° C. to prevent formation of RNA secondary structure. Examples of reverse transcriptases that are relatively stable at these temperatures are SuperScript II Reverse Transcriptase (Life Technologies, Inc.), AMV Reverse Transcriptase (Boehringer Mannheim) and RetroAmp Reverse Transcriptase (Epicentre). Rapidly growing tissues, or rapidly dividing cells are preferably used as mRNA sources.

The present invention also provides subsequences of the polynucleotides of the present invention. A variety of subsequences can be obtained using primers which selectively hybridize under stringent conditions to at least two sites within a polynucleotide of the present invention, or to two sites within the nucleic acid which flank and comprise a polynucleotide of the present invention, or to a site within a polynucleotide of the present invention and a site within the nucleic acid which comprises it. Primers are chosen to selectively hybridize, under stringent hybridization conditions, to a polynucleotide of the present invention. Generally, the primers are complementary to a subsequence of the target nucleic acid which they amplify. As those skilled in the art will appreciate, the sites to which the primer pairs will selectively hybridize are chosen such that a single contiguous nucleic acid can be formed under the desired amplification conditions. In optional embodiments, the primers will be constructed so that they selectively hybridize under stringent conditions to a sequence (or its complement) within the target nucleic acid which comprises the codon encoding the carboxy or amino terminal amino acid residue (i.e., the 3' terminal coding region and 5' terminal coding region, respectively) of the polynucleotides of the present invention. Optionally within these embodiments, the primers will be constructed to selectively hybridize entirely within the coding region of the target polynucleotide of the present invention such that the product of amplification of a cDNA target will consist of the coding region of that cDNA. The primer length in nucleotides is selected from the group of integers consisting of from at least 15 to 50. Thus, the primers can be at least 15, 18, 20, 25, 30, 40, or 50 nucleotides in length. Those of skill will recognize that a lengthened primer sequence can be employed to increase specificity of binding (i.e., annealing) to a target sequence. A non-annealing sequence at the 5' end of a primer (a "tail") can be added, for example, to introduce a cloning site at the terminal ends of the amplicon.

The amplification products can be translated using expression systems well known to those of skill in the art and as discussed, infra. The resulting translation products can be confirmed as polypeptides of the present invention by, for example, assaying for the appropriate catalytic activity (e.g., specific activity and/or substrate specificity), or verifying the presence of one or more linear epitopes which are specific to a polypeptide of the present invention. Methods for protein synthesis from PCR derived templates are known in the art and available commercially. See, e.g., Amersham Life Sciences, Inc, Catalog '97, p.354.

Methods for obtaining 5' and/or 3' ends of a vector insert are well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego), pp. 28–38 (1990)); see also, U.S. Pat. No. 5,470,722, and *Current Protocols in Molecular Biology*, Unit 15.6, Ausubel, et al., Eds, Greene Publishing and Wiley-Interscience, New York (1995); Frohman and Martin, *Techniques* 1:165 (1989).

C. Polynucleotides Which Selectively Hybridize to a Polynucleotide of (A) or (B)

As indicated in (c), above, the present invention provides isolated nucleic acids comprising polynucleotides of the present invention, wherein the polynucleotides selectively hybridize, under selective hybridization conditions, to a polynucleotide of sections (A) or (B) as discussed above. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library. In some embodiments, the polynucleotides are genomic or cDNA sequences isolated or otherwise complementary to a cDNA from a dicot or monocot nucleic acid library. Exemplary species of monocots and dicots include, but are not limited to: corn, canola, soybean, cotton, wheat, sorghum, sunflower, oats, sugar cane, millet, barley, and rice. Optionally, the cDNA library comprises at least 80% full-length sequences, preferably at least 85% or 90% full-length sequences, and more preferably at least 95% full-length sequences. The cDNA libraries can be normalized to increase the representation of rare sequences. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

D. Polynucleotides Having a Specific Sequence Identity with the Polynucleotides of (A), (B) or (C)

As indicated in (d), above, the present invention provides isolated nucleic acids comprising polynucleotides of the present invention, wherein the polynucleotides have a specified identity at the nucleotide level to a polynucleotide as disclosed above in sections (A), (B), or (C), above. The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least 70%, 75%, 80%, 81%, 82%, 83%, 84%, 85%, 86%, 87%, 88%, 89%, 90%, 91%, 92%, 93%, 94%, 95%, 96%, 97%, 98%, or 99%.

Optionally, the polynucleotides of this embodiment will encode a polypeptide that will share an epitope with a polypeptide encoded by the polynucleotides of sections (A), (B), or (C). Thus, these polynucleotides encode a first polypeptide which elicits production of antisera comprising antibodies which are specifically reactive to a second polypeptide encoded by a polynucleotide of (A), (B), or (C). However, the first polypeptide does not bind to antisera raised against itself when the antisera has been fully immunosorbed with the first polypeptide. Hence, the polynucleotides of this embodiment can be used to generate antibodies for use in, for example, the screening of expression libraries for nucleic acids comprising polynucleotides of (A), (B), or (C), or for purification of, or in immunoassays for, polypeptides encoded by the polynucleotides of (A), (B), or (C). The polynucleotides of this embodiment embrace nucleic acid sequences. which can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5–100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT patent publication Nos. 91/17271, 91/18980, 91/19818, and 93/08278. Other systems for generating libraries of peptides have aspects of both in vitro chemical synthesis and recombinant methods. See, PCT Patent publication Nos. 92/05258, 92/14843, and 96/19256. See also, U.S. Pat. Nos. 5,658,754; and 5,643,768. Peptide display libraries, vectors, and screening kits are commercially available from such suppliers as Invitrogen (Carlsbad, Calif.).

E. Polynucleotides Encoding a Protein Having a Subsequence from a Prototype Polypeptide and is Cross-Reactive to the Prototype Polypeptide As indicated in (e), above, the present invention provides isolated nucleic acids comprising polynucleotides of the present invention, wherein the polynucleotides encode a protein having a subsequence of contiguous amino acids from a prototype polypeptide of the present invention such as are provided in (a),; above. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45, or 50, contiguous amino acids from the prototype polypeptide. Further, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The proteins encoded by polynucleotides of this embodiment, when presented as an immunogen, elicit the production of polyclonal antibodies which specifically bind to a prototype polypeptide such as but not limited to, a polypeptide encoded by the polynucleotide of (a) or (b), above. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art. Exemplary immunoassay formats include ELISA,. competitive immunoassays, radioimmunoassays, Western blots, indirect immunofluorescent assays and the like.

In a preferred assay method, fully immunosorbed and pooled antisera which is elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen. Accordingly, the proteins of the present invention embrace allelic variants, conservatively modified variants, and minor recombinant modifications to a prototype polypeptide.

A polynucleotide of the present invention optionally encodes a protein having a molecular weight as the non-glycosylated protein within 20% of the molecular weight of the full-length non-glycosylated polypeptides of the present invention. Molecular weight can be readily determined by SDS-PAGE under reducing conditions. Optionally, the molecular weight is within 15% of a full length polypeptide of the present invention, more preferably within 10% or 5%, and most preferably within 3%, 2%, or 1% of a full length polypeptide of the present invention.

Optionally, the polynucleotides of this embodiment will encode a protein having a specific enzymatic activity at least 50%, 60%, 80%, or 90% of a cellular extract comprising the native, endogenous full-length polypeptide of the present invention. Further, the proteins encoded by polynucleotides of this embodiment will optionally have a substantially similar affinity constant ($K_m$) and/or catalytic activity (i.e., the microscopic rate constant, $k_{cat}$) as the native endogenous, full-length protein. Those of skill in the art will recognize that $k_{cat}/K_m$ value determines the specificity for competing substrates and is often referred to as the specificity constant. Proteins of this embodiment can have a $k_{cat}/K_m$ value at least 10% of a full-length polypeptide of the present invention as determined using the endogenous substrate of that polypeptide. Optionally, the $k_{cat}/K_m$ value will be at least 20%, 30%, 40%, 50%, and most preferably at least 60%, 70%, 80%, 90%, or 95% the $k_{cat}/K_m$ value of the full-length polypeptide of the present invention. Determination of $k_{cat}$, $K_m$, and $k_{cat}/K_m$ can be determined by any number of means well known to those of skill in the art. For example, the initial rates (i.e., the first 5% or less of the reaction) can be determined using rapid mixing and sampling techniques (e.g., continuous-flow, stopped-flow, or rapid quenching techniques), flash photolysis, or relaxation methods (e.g., temperature jumps) in conjunction with such exemplary methods of measuring as spectrophotometry, spectrofluorimetry, nuclear magnetic resonance, or radioactive procedures. Kinetic values are conveniently obtained using a Lineweaver-Burk or Eadie-Hofstee plot.

F. Polynucleotides Complementary to the Polynucleotides of (A)–(E)

As indicated in (f), above, the present invention provides isolated nucleic acids comprising polynucleotides complementary to the polynucleotides of paragraphs A–E, above. As those of skill in the art will recognize, complementary sequences base-pair throughout the entirety of their length with the polynucleotides of sections (A)–(E) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

G. Polynucleotides Which are Subsequences of the Polynucleotides of (A)–(F)

As indicated in (g), above, the present invention provides isolated nucleic acids comprising polynucleotides which comprise at least 15 contiguous bases from the polynucleotides of sections (A) through (F) as discussed above. The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 20, 25, 30, 35, 40, 45, 50, 55, 60, 65, 70, 75, or 100 contiguous nucleotides in length from the polynucleotides of (A)–(F). Optionally, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The subsequences of the present invention can comprise structural characteristics of the sequence from which it is derived. Alternatively, the subsequences can lack certain structural characteristics of the larger sequence from which it is derived such as a poly (A) tail. Optionally, a subsequence from a polynucleotide encoding a polypeptide having at least one linear epitope in common with a prototype polypeptide sequence as provided in (a), above, may encode an epitope in common with the prototype sequence. Alternatively, the subsequence may not encode an epitope in common with the prototype sequence but can be used to isolate the larger sequence by, for example, nucleic acid hybridization with the sequence from which it's derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot. In preferred embodiments the monocot is Zea mays.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. A polynucleotide of the present invention can be attached to a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known and extensively described in the art. For a description of various nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

A. Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library. While isolation of RNA, and construction of cDNA and genomic libraries is well known to those of ordinary skill in the art, the following highlights some of the methods employed.

A1. mRNA Isolation and Purification

Total RNA from plant cells comprises such nucleic acids as mitochondrial RNA, chloroplastic RNA, rRNA, tRNA, hnRNA and mRNA. Total RNA preparation typically involves lysis of cells and removal of organelles and proteins, followed by precipitation of nucleic acids. Extraction of total RNA from plant cells can be accomplished by a variety of means. Frequently, extraction buffers include a strong detergent such as SDS and an organic denaturant such as guanidinium isothiocyanate, guanidine hydrochloride or phenol. Following total RNA isolation, poly(A)$^+$ mRNA is typically purified from the remainder NA using oligo(dT) cellulose. Exemplary total RNA and mRNA isolation protocols are escribed in *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'–3' (Paoli Inc., Pa.). See also, U.S. Pat. Nos. 5,614,391; and, 5,459,253. The mRNA can be fractionated into populations with size ranges of about 0.5, 1.0, 1.5, 2.0, 2.5 or 3.0 kb. The cDNA synthesized for each of these fractions can be size selected to the same size range as its mRNA prior to vector insertion. This method helps eliminate truncated cDNA formed by incompletely reverse transcribed mRNA.

A2. Construction of a cDNA Library

Construction of a cDNA library generally entails five steps. First, first strand cDNA synthesis is initiated from a poly(A)$^+$ mRNA template using a poly(dT) primer or random hexanucleotides. Second, the resultant RNA-DNA hybrid is converted into double stranded cDNA, typically by reaction with a combination of RNAse H and DNA polymerase I (or Klenow fragment). Third, the termini of the double stranded cDNA are ligated to adaptors. Ligation of the adaptors can produce cohesive ends for cloning. Fourth, size selection of the double stranded cDNA eliminates excess adaptors and primer fragments, and eliminates partial cDNA molecules due to degradation of mRNAs or the failure of reverse transcriptase to synthesize complete first strands. Fifth, the cDNAs are ligated into cloning vectors and packaged. cDNA synthesis protocols are well known to the skilled artisan and are described in such standard references as: *Plant Molecular Biology. A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). cDNA synthesis kits are available from a variety of commercial vendors such as Stratagene or Pharmacia.

A number of cDNA synthesis protocols have been described which provide substantially pure full-length cDNA libraries. Substantially pure full-length cDNA libraries are constructed to comprise at least 90%, and more preferably at least 93% or 95% full-length inserts amongst clones containing inserts. The length of insert in such libraries can be from 0 to 8, 9, 10, 11, 12, 13, or more kilobase pairs. Vectors to accommodate inserts of these sizes are known in the art and available commercially. See, e.g., Stratagene's lambda ZAP Express (cDNA cloning vector with 0 to 12 kb cloning capacity).

An exemplary method of constructing a greater than 95% pure full-length cDNA library is described by Carninci et al., *Genomics*, 37:327–336 (1996). In that protocol, the cap-structure of eukaryotic mRNA is chemically labeled with biotin. By using streptavidin-coated magnetic beads, only the full-length first-strand cDNA/mRNA hybrids are selectively recovered after RNase I treatment. The method provides a high yield library with an unbiased representation of the starting mRNA population. Other methods for producing full-length libraries are known in the art. See, e.g., Edery et al., *Mol. Cell Biol.*, 15(6):3363–3371 (1995); and, PCT Application WO 96/34981.

A3. Normalized or Subtracted cDNA Libraries

A non-normalized cDNA library represents the mRNA population of the tissue it was made from. Since unique clones are out-numbered by clones derived from highly expressed genes their isolation can be laborious. Normalization of a cDNA library is the process of creating a library in which each clone is more equally represented.

A number of approaches to normalize cDNA libraries are known in the art. One approach is based on hybridization to genomic DNA. The frequency of each hybridized cDNA in the resulting normalized library would be proportional to that of each corresponding gene in the genomic DNA. Another approach is based on kinetics. If cDNA reannealing follows second-order kinetics, rarer species anneal less rapidly and the remaining single-stranded fraction of cDNA becomes progressively more normalized during the course of the hybridization. Specific loss of any species of cDNA, regardless of its abundance, does not occur at any Cot value. Construction of normalized libraries is described in Ko, *Nucl. Acids. Res.*, 18(19):5705–5711 (1990); Patanjali et al., *Proc. Natl. cad. U.S.A.*, 88:1943–1947 (1991); U.S. Pat. Nos. 5,482,685, and 5,637,685. In an exemplary method described by Soares et al., normalization resulted in reduction of the abundance of clones from a range of four orders of magnitude to a narrow range of only 1 order of magnitude. *Proc. Natl. Acad. Sci. USA*, 91:9228–9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized cDNA pool is enriched for sequences unique to that pool. See, Foote et al. in, *Plant Molecular Biology: A Laboratory Manual*, Clark, Ed., Springer-Verlag, Berlin (1997); Kho and Zarbl, *Technique*, 3(2):58–63 (1991); Sive and St. John, *Nucl. Acids Res.*, 16(22):10937 (1988); *Current Protocols in Molecular Biology*, Ausubel, et al., Eds., Greene Publishing and Wiley-Interscience, New York (1995); and, Swaroop et al., *Nucl. Acids Res.*, 19)8): 1954 (1991). cDNA subtraction kits are commercially available. See, e.g., PCR-Select (Clontech, Palo Alto, Calif.).

A4. Construction of a Genomic Library

To construct genomic libraries, large segments of genomic DNA are generated by fragmentation, e.g. using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook, et al., *Molecular Cloning: A Laboratory Manual*, 2nd Ed., Cold Spring Harbor Laboratory Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and .Wiley-Interscience, New York (1995); *Plant Molecular Biology: A Laboratory Manual*, Clark, Ed., Springer-Verlag, Berlin (1997). Kits for construction of genomic libraries are also commercially available.

A5. Nucleic Acid Screening and Isolation Methods

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100 percent; however, it should be understood that minor sequence variations in the probes and primers may be compensated for by reducing the stringency of the hybridization and/or wash medium.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, Sambrook, and Ausubel, as well as Mullis et al., U.S. Pat. No. 4,683,202 (1987); and, *PCR Protocols A Guide to Methods and Applications*, Innis et al., Eds., Academic Press Inc., San Diego, Calif. (1990). Commercially available kits for genomic PCR amplification are known in the art. See, 25 e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques*, 22(3): 481–486 (1997). In that method, a primer pair is synthesized with one primer annealing to the 5' end of the sense strand of the desired cDNA and the other primer to the vector. Clones are pooled to allow large-scale screening. By this procedure, the longest possible clone is identified amongst candidate clones. Further, the PCR product is used solely as a diagnostic for the presence of the desired cDNA and does not utilize the PCR product itself. Such methods are particularly effective in combination with a full-length cDNA construction methodology, above.

B. Synthetic Methods for Constructing Nucleic Acids

The isolated nucleic acids of the present invention can also be prepared by direct chemical synthesis by methods such as the phosphotriester method of Narang et al., *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.* 22: 1859–1862 (1981); the solid phase phosphoramidite triester method described by Beaucage and Caruthers, *Tetra. Letts.* 22(20): 1859–1862 (1981), e.g., using an automated synthesizer, e.g., as described in Needham-VanDevanter et al., *Nucleic Acids Res.*, 12: 6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is best employed for sequences of about 100 bases or less, longer sequences may be obtained by the ligation of shorter sequences.

Recombinant Expression Cassettes

The present invention further provides recombinant expression cassettes comprising a nucleic acid of the present invention. A nucleic acid sequence coding for the desired polypeptide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'- promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter, and other transcription initiation regions from various plant genes known to those of skill. One exemplary promoter is the ubiquitin promoter, which can be used to drive expression of the present invention in embryos or embryogenic callus, particularly in maize.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter which is inducible by hypoxia or cold stress, the Hsp70 promoter which is inducible by heat stress, and the PPDK promoter hich is inducible by light.

Examples of promoters under developmental control include promoters that initiate transcription only, or preferentially, in certain tissues, such as leaves, roots, fruit, seeds, or flowers. Exemplary promoters include the anther specific promoter 5126 (U.S. Pat. Nos. 5,689,049 and 5,689,051), glob-1 promoter, and ganmma-zein promoter. The operation of a promoter may also vary depending on its location in the genome. Thus, an inducible promoter may become fully or partially constitutive in certain locations.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue. Thus, in some embodiments, the nucleic acid construct will comprise a promoter functional in a plant cell, such as in *Zea mays*, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a gene of the present invention so as to control the expression of the gene. Gene expression can be modulated under conditions suitable for plant growth so as to alter the total concentration and/or alter the composition of the polypeptides of the present invention in plant cell. Thus, the present invention provides compositions, and methods for making, heterologous promoters and/or enhancers operably linked to a native, endogenous (i.e., non-heterologous) form of a polynucleotide of the present invention.

Methods for identifying promoters with a particular expression pattern, in terms of, e.g., tissue type, cell type, stage of development, and/or environmental conditions, are well known in the art. See, e.g., *The Maize Handbook*, Chapters 114–115, Freeling and Walbot, Eds., Springer, New York (1994); *Corn and Corn Improvement*, $3^{rd}$ edition, Chapter 6, Sprague and Dudley, Eds., American Society of Agronomy, Madison, Wis. (1988). A typical step in promoter isolation methods is identification of gene products that are expressed with some degree of specificity in the target tissue. Amongst the range of methodologies are: differential hybridization to cDNA libraries; subtractive hybridization; differential display; differential 2-D protein gel electrophoresis; DNA probe arrays; and isolation of proteins known to be expressed with some specificity in the target tissue. Such methods are well known to those of skill in the art. Commercially available products for identifying promoters are known in the art such as Clontech's (Palo Alto, Calif.) Universal GenomeWalker Kit.

For the protein-based methods, it is helpful to obtain the amino acid sequence for at least a portion of the identified protein, and then to use the protein sequence as the basis for preparing a nucleic acid that can be used as a probe to identify either genomic DNA directly, or preferably, to identify a cDNA clone from a library prepared from the target tissue. Once such a cDNA clone has been identified, that sequence can be used to identify the sequence at the 5' end of the transcript of the indicated gene. For differential hybridization, subtractive hybridization and differential display, the nucleic acid sequence identified as enriched in the target tissue is used to identify the sequence at the 5' end of the transcript of the indicated gene. Once such sequences are identified, starting either from protein sequences or nucleic acid sequences, any of these sequences identified as being from the gene transcript can be used to screen a genomic library prepared from the target organism. Methods for identifying and confirming the transcriptional start site are well known in the art.

In the process of isolating promoters expressed under particular environmental conditions or stresses, or in specific tissues, or at particular developmental stages, a number of genes are identified that are expressed under the desired circumstances, in the desired tissue, or at the desired stage. Further analysis will reveal expression of each particular gene in one or more other tissues of the plant. One can identify a promoter with activity in the desired tissue or condition but that does not have activity in any other common tissue.

To identify the promoter sequence, the 5' portions of the clones described here are analyzed for sequences characteristic of promoter sequences. For instance, promoter sequence elements include the TATA box consensus sequence (TATAAT), which is usually an AT-rich stretch of 5–10 bp located approximately 20 to 40 base pairs upstream of the transcription start site. Identification of the TATA box is well known in the art.

For example, one way to predict the location of this element is to identify the transcription start site using standard RNA-mapping techniques such as primer extension, S1 analysis, and/or RNase protection. To confirm the presence of the AT-rich sequence, a structure-function analysis can be performed involving mutagenesis of the putative region and quantification of the mutation's effect on expression of a linked downstream reporter gene. See, e.g., *The Maize Handbook*, Chapter 114, Freeling and Walbot, Eds., Springer, New York, (1994).

In plants, further upstream from the TATA box, at positions −80 to −100, there is typically a promoter element (i.e., the CAAT box) with a series of adenines surrounding the trinucleotide G (or T) N G. J. Messing et al., in *Genetic Engineering in Plants*, Kosage, Meredith and Hollaender, Eds., pp. 221–227 1983. In maize, there is no well conserved CAAT box but there are several short, conserved protein-binding motifs upstream of the TATA box. These include motifs for the trans-acting transcription factors involved in light regulation, anaerobic induction, hormonal regulation, or anthocyanin biosynthesis, as appropriate for each gene.

Once promoter and/or gene sequences are known, a region of suitable size is selected from the genomic DNA that is 5' to the transcriptional start, or the translational start site, and such sequences are then linked to a coding sequence. If the transcriptional start site is used as the point of fusion, any of a number of possible 5' untranslated regions can be used in between the transcriptional start site and the partial coding sequence. If the translational start site at the 3' end of the specific promoter is used, then it is linked directly to the methionine start codon of a coding sequence.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8: 4395–4405 (1988); Callis et al., *Genes Dev.* 1: 1183–1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, New York (1994).

The vector comprising the sequences from a polynucleotide of the present invention will typically comprise a marker gene which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfiuron.

Typical vectors useful for expression of genes in higher plants are well known in the art and include vectors derived from the tumor-inducing (Ti) plasmid of *Agrobacterium tumefaciens* described by Rogers et al., Meth. in Enzymol., 153:253–277 (1987). These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl et al., Gene, 61: 1–11 (1987) and Berger et al., *Proc. Natl. Acad. Sci. U.S.A.*, 86:8402–8406 (1989). Another useful vector herein is plasmid pBI101.2 that is available from Clontech Laboratories, Inc. (Palo Alto, Calif.).

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to inhibit gene expression in plants. To accomplish this, a nucleic acid segment from the desired gene is cloned and operably linked to a promoter such that the anti-sense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy et al., *Proc. Nat'l. Acad. Sci.* (*USA*) 85: 8805–8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2: 279–289 (1990) and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., *Nature* 334: 585–25 591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleotide which was capable of activating cleavage (*J Am Chem Soc* (1987) 109:1241–1243). Meyer, R. B., et al., *J Am Chem Soc* (1989) 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Home, et al., *J Am Chem Soc* (1990) 112:2435–2437. Use of N4, N4-ethanocytosine as an alkylating agent to crosslink to single-stranded oligonucleotides has also been described by Webb and Matteucci, *J Am Chem Soc* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681941.

Proteins

The isolated proteins of the present invention comprise a polypeptide having at least 10 amino acids encoded by any one of the polynucleotides of the present invention as discussed more fully, above, or polypeptides which are conservatively modified variants thereof. The proteins of the present invention or variants thereof can comprise any number of contiguous amino acid residues from a polypeptide of the present invention, wherein that number is selected from the group of integers consisting of from 10 to the number of residues in a full-length polypeptide of the present invention. Optionally, this subsequence of contiguous amino acids is at least 15, 20, 25, 30, 35, or 40 amino acids in length, often at least 50, 60, 70, 80, or 90 amino acids in length. Further, the number of such subsequences can be any integer selected from the group consisting of from 1 to 20, such as 2, 3, 4, or 5.

The present invention further provides a protein comprising a polypeptide having a specified sequence identity with a polypeptide of the present invention. The percentage of sequence identity is an integer selected from the group consisting of from 50 to 99. Exemplary sequence identity values include 60%, 65%, 70%, 75%, 80%, 85%, 86%, 87%, 88%, 89%, 90%, 91%, 92%, 93%, 94%, 95%, 96%, 97%, 98% and 99%. Sequence identity can be determined using, for example, the GAP or BLAST algorithms.

As those of skill will appreciate, the present invention includes catalytically active polypeptides of the present invention (i.e., enzymes). Catalytically active polypeptides have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay as discussed, infra. Thus, the proteins of the present invention can be employed as immunogens for constructing antibodies immunoreactive to a protein of the present invention for such exemplary utilities as immunoassays or protein purification techniques.

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located purification sequences. Restriction sites or termination codons can also be introduced.

A. Expression in Prokaryotes

Prokaryotic cells may be used as hosts for expression. Prokaryotes most frequently are represented by various strains of E. coli; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., *Nature* 198:1056 (1977)), the tryptophan (trp) promoter system (Goeddel et al., *Nucleic Acids Res.* 8:4057 (1980)) and the lambda derived P L promoter and N-gene ribosome binding site (Shimatake et al., *Nature* 292:128 (1981)). The inclusion of selection markers in DNA vectors transfected in E. coli is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using Bacillus sp. and Salmonella (Palva, et al., *Gene* 22: 229–235 (1983); Mosbach, et al., *Nature* 302: 543–545 (1983)).

B. Expression in Eukaryotes

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, F., et al., *Methods in Yeast Genetics*, Cold Spring Harbor Laboratory (1982) is a well recognized work describing the various methods available to produce the protein in yeast. Two widely utilized yeast for production of eukaryotic proteins are *Saccharomyces cerevisiae* and *Pichia pastoris*. Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al., *Immunol. Rev.* 89: 49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and Drosophila cell lines such as a Schneider cell line (See, Schneider, *J. Embryol. Exp. Morphol.* 27: 353–365 (1987).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., *J. Virol.* 45: 773–781 (1983)). Additionally, gene sequences to control replication in the host cell may be incorporated into the vector such as those found in bovine papilloma virus type-vectors. Saveria-Campo, M., Bovine Papilloma Virus DNA a Eukaryotic Cloning Vector in *DNA Cloning Vol. II a Practical Approach*, D. M. Glover, Ed., IRL Press, Arlington, Va. pp. 213–238 (1985).

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for effective transformation/transfection may be employed.

A. Plant Transformation

A DNA sequence coding for the desired polypeptide of the present invention, for example a cDNA or a genomic sequence encoding a full length protein, will be used to construct a recombinant expression cassette which can be introduced into the desired plant.

Isolated nucleic acids of the present invention can be introduced into plants according to techniques known in the art. Generally, recombinant expression cassettes as described above and suitable for transformation of plant cells are prepared. The isolated nucleic acids of the present invention can then be used for transformation. In this manner, genetically modified plants, plant cells, plant tissue, seed, and the like can be obtained. Transformation protocols may vary depending on the type of plant cell, i.e. monocot or dicot, targeted for transformation. Suitable methods of transforming plant cells include microinjection (Crossway et al. (1986) Biotechniques 4:320–334), electroporation (Riggs et al (1986) *Proc. Natl. Acad. Sci. USA* 83:5602–5606, Agrobacterium mediated transformation (Hinchee et al. (1988) *Biotechnology* 6:915–921), direct gene transfer (Paszkowski et al (1984) *EMBO J.* 3:2717–2722), and ballistic particle acceleration (see, for example, Sanford et al. U.S. Pat. No. 4,945,050; Tomes et al. "Direct DNA Transfer into Intact Plant Cells via Microprojectile Bombardment" In Gamborg and Phillips (Eds.) *Plant Cell, Tissue and Organ Culture: Fundamental Methods*, Springer-Verlag, Berlin (1995); and McCabe et al. (1988) *Biotechnology* 6:923–926). Also see, Weissinger et al. (1988) *Annual Rev. Genet.* 22:421–477; Sanford et al. (1987) *Particulate Science and Technology* 5:27–37 (onion); Christou et al. (1988) *Plant Phisiol.* 87:671–674 (soybean); McCabe et al. (1988) *Bio/Technology* 6:923–926 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes et al. "Direct DNA Transfer into Intact Plant Cells via Microprojectile Bombardment" In Gamborg and Phillips (Eds.) *Plant Cell, Tissue and Organ Culture: Fundamental Methods*, Springer-Verlag, Berlin (1995) (maize); Klein et al. (1988) *Plant Physiol.* 91:440–444 (maize) Fromm et al. (1990) *Biotechnology* 8:833–839 (maize); Hooykaas-Van Slogteren & Hooykaas (1984) *Nature* (London) 311:763–764; Bytebier et al. (1987) *Proc. Natl. Acad. Sci. USA* 84:5345–5349 (Liliaceae); De Wet et al. (1985) In *The Experimental Manipulation of Ovule Tissues* ed. G. P. Chapman et al. pp. 197–209. Longman, N.Y. (pollen); Kaeppler et al. (1990) *Plant Cell Reports* 9:415–418; and Kaeppler et al. (1992) *Theor. Appl. Genet.* 84:560–566 (whisker-mediated transformation); D'Halluin et al. (1992) *Plant Cell* 4:1495–1505 (electroporation); LI et al. (1993) *Plant Cell Reports* 12:250–255 and Christou and Ford (1995) *Annals of Botany* 75:745–750 (maize via *Agrobacterium tumefaciens*); all of which are herein incorporated by reference.

The cells which have been transformed may be grown into plants in accordance with conventional ways. See, for example, McCormick et al. (1986) *Plant Cell Reports*, 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

B. Transfection of Prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides. Analysis, Synthesis, Biology.* Vol. 2: *Special Methods in Peptide Synthesis*, Part A.; Merrifield, et al., *J. Am. Chem. Soc.* 85: 2149–2156 (1963), and Stewart et al., *Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide)) is known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

Transgenic Plant Regeneration

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al.,

*Protoplasts Isolation and Culture, Handbook of Plant Cell Culture*, Macmillilan Publishing Company, New York, pp. 124–176 (1983); and Binding, *Regeneration of Plants, Plant Protoplasts*, CRC Press, Boca Raton, pp. 21–73 (1985).

The regeneration of plants containing the foreign gene introduced by Agrobacterium from leaf explants can be achieved as described by Horsch et al., *Science*, 227:1229–1231 (1985). In this procedure, transformants are grown in the presence of a selection agent and in a medium that induces the regeneration of shoots in the plant species being transformed as described by Fraley et al., *Proc. Natl. Acad. Sci. (U.S.A.)*, 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38: 467–486 (1987). The regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). This regeneration and growth process includes the steps of selection of transformnant cells and shoots, rooting the transformant shoots and growth of the plantlets in soil. For maize cell culture and regeneration see generally, *The Maize Handbook*, Freeling and Walbot, Eds., Springer, New York (1994); *Corn and Corn Improvement*, $3^{rd}$ edition, Sprague and Dudley Eds., American Society of Agronomy, Madison, Wis. (1988).

One of skill will recognize that after the recombinant expression cassette is stably corporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non- transgenic plant are also contemplated.

Modulating Polypeptide Levels and/or Composition

The present invention further provides a method for modulating (i.e., increasing or decreasing) the concentration or ratio of the polypeptides of the present invention in a plant or part thereof. Modulation can be effected by increasing or decreasing the concentration and/or the the ratio of the polypeptides of the present invention in a plant. The method comprises introducing into a plant cell with a recombinant expression cassette comprising a polynucleotide of the present invention as described above to obtain a transformed plant cell, culturing the transformed plant cell under plant cell growing conditions, and inducing or repressing expression of a polynucleotide of the present. invention in the plant for a time sufficient to modulate concentration and/or the ratios of the polypeptides in the plant or plant part.

In some embodiments, the concentration and/or ratios of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or ratios of polypeptides of the present invention in the plant. Plant forming conditions are well known in the art and discussed briefly, supra.

In general, concentration or the ratios of the polypeptides is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In preferred embodiments, the polypeptides of the present invention are modulated in monocots, particularly maize.

Molecular Markers

The present invention provides a method of genotyping a plant comprising a polynucleotide of the present invention. Optionally, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Texas, pp.7–21.

The particular method of genotyping in the present invention may employ any number of molecular marker analytic techniques such as, but not limited to, restriction fragment length polymorphisms (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the present invention.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention. Typically, these probes are cDNA probes or restriction-enzyme treated (e.g., Pst I) genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, *Nucleic Acids Res.* 15:8125 (1987)) and the 7-methylguanosine cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host such as to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12: 387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. WO 97/20078. See also, Zhang, J.-H., et al. *Proc. Natl. Acad. Sci. USA* 94:4504–4509 (1997). Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be a decreased $K_m$ and/or increased $K_{cat}$ over the wild-type protein as provided herein. In other embodiments, a protein or polynculeotide generated from sequence shuffling will have a ligand binding affinity greater than the non-shuffled wild-type polynucleotide. The increase in such properties can be at least 110%, 120%, 130%, 140% or at least 150% of the wild-type value.

Generic and Consensus Sequences

Polynucleotides and polypeptides of the present invention further include those having: (a) a generic sequence of at least two homologous polynucleotides or polypeptides, respectively, of the present invention; and, (b) a consensus sequence of at least three homologous polynucleotides or polypeptides, respectively, of the present invention. The generic sequence of the present invention comprises each species of polypeptide or polynucleotide embraced by the generic polypeptide or polynucleotide, sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phylums, or kingdoms. For example, a polynucleotide having a consensus sequences from a gene family of *Zea mays* can be used to generate antibody or nucleic acid probes or primers to other Gramineae species such as wheat, rice, or sorghum. Alternatively, a polynucleotide having a consensus sequence generated from orthologous genes can be used to identify or isolate orthologs of other taxa. Typically, a polynucleotide having a consensus sequence will be at least 9, 10, 15, 20, 25, 30, or 40 amino acids in length, or 20, 30, 40, 50, 100, or 150 nucleotides in length. As those of skill in the art are aware, a conservative amino acid substitution can be used for amino acids which differ amongst aligned sequence but are from the same conservative substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous, or paralogous sequences as provided herein. Optionally, similar sequences used in generating a consensus or generic sequence are identified using the BLAST algorithm's smallest sum probability (P(N)). Various suppliers of sequence-analysis software are listed in chapter 7 of *Current Protocols in Molecular Biology*, F. M. Ausubel et al., Eds., Current Protocols, a joint venture between Greene Publishing Associates, Inc. and John Wiley & Sons, Inc. (Supplement 30). A polynucleotide sequence is considered similar to a reference sequence if the smallest sum probability in a comparison of the test nucleic acid to the reference nucleic acid is less than about 0.1, more preferably less than about 0.01, or 0.001, and most preferably less than about 0.0001, or 0.00001. Similar polynucleotides can be aligned and a consensus or generic sequence generated using multiple sequence alignment software available from a number of commercial suppliers such as the Genetics Computer Group's (Madison, Wis.) PILEUP software, Vector NTI's (North Bethesda, Md.) ALIGNX, or Genecode's (Ann Arbor, Mich.) SEQUENCHER. Conveniently, default parameters of such software can be used to generate consensus or generic sequences.

Assays for Compounds that Modulate Enzymatic Activity or Expression

The present invention also provides means for identifying compounds that bind to (e.g., substrates), and/or increase or decrease (i.e., modulate) the enzymatic activity of, catalytically active polypeptides of the present invention. The method comprises contacting a polypeptide of the present invention with a compound whose ability to bind to or modulate enzyme activity is to be determined. The polypeptide employed will have at least 20%, preferably at least 30% or 40%, more preferably at least 50% or 60%, and most preferably at least 70% or 80% of the specific activity of the native, full-length polypeptide of the present invention (e.g., enzyme). Generally, the polypeptide will be present in a range sufficient to determine the effect of the compound, typically about 1 nM to 10 $\mu$M. Likewise, the compound will be present in a concentration of from about 1 nM to 10 $\mu$M. Those of skill will understand that such factors as enzyme concentration, ligand concentrations (i.e., substrates, products, inhibitors, activators), pH, ionic strength, and temperature will be controlled so as to obtain useful kinetic data and determine the presence of absence of a compound that binds or modulates polypeptide activity. Methods of measuring enzyme kinetics is well known in the art. See, e.g., Segel, *Biochemical Calculations*, $2^{nd}$ ed., John Wiley and Sons, New York (1976).

Although the present invention has been described in some detail by way of illustration and example for purposes of clarity of understanding, it will be obvious that certain changes and modifications may be practiced within the scope of the appended claims.

EXAMPLE 1

This example describes the construction of the cDNA libraries.

Total RNA Isolation

The RNA for SEQ ID NO: 1 was isolated from maize log phase suspension cells (Black Mexican Sweet) treated with Calcimycin (Calbiochem, catalog no: 100105) to induce mass apoptosis. Total RNA was isolated from corn tissues with TRIZOL Reagent (Life Technology Inc. Gaithersburg, Md.) using a modification of the guanidine isothiocyanate/acid-phenol procedure described by Chomczynski and Sacchi (Chomczynski, P., and Sacchi, N. *Anal. Biochem.* 162, 156 (1987)). In brief, plant tissue samples were pulverized in liquid nitrogen before the addition of the TRIZOL Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

Poly(A)+RNA Isolation

The selection of poly(A)+RNA from total RNA was performed using POLYATTRACT system (Promega Corporation. Madison, Wis.). In brief, biotinylated oligo(dT) primers were used to hybridize to the 3' poly(A) tails on mRNA. The hybrids were captured using streptavidin coupled to paramagnetic particles and a magnetic separation stand. The mRNA was washed at high stringency conditions and eluted by RNase-free deionized water.

cDNA Library Construction cDNA synthesis was performed and unidirectional cDNA libraries were constructed using the SUPERSCRIPT Plasmid System (Life Technology Inc. Gaithersburg, Md.). The first stand of cDNA was synthesized by priming an oligo (dT) primer containing a Not I site. The reaction was catalyzed by SUPERSCRIPT Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between of Not I and Sal I sites.

EXAMPLE 2

This example describes cDNA sequencing and library subtraction.

Sequencing Template Preparation

Individual colonies were picked and DNA was prepared either by PCR with M13 forward primers and M13 reverse primers, or by plasmid isolation. All the cDNA clones were sequenced using M13 reverse primers.

Q-bot Subtraction Procedure cDNA libraries subjected to the subtraction procedure were plated out on 22×22 cm$^2$ agar plate at density of about 3,000 colonies per plate. The plates were incubated in a 37° C. incubator for 12–24 hours. Colonies were picked into 384-well plates by a robot colony picker, Q-bot (GENETIX Limited). These plates were incubated overnight at 37° C.

Once sufficient colonies were picked, they were pinned onto 22×22 cm$^2$ nylon membranes using Q-bot. Each membrane contained 9,216 colonies or 36,864 colonies. These membranes were placed onto agar plate with appropriate antibiotic. The plates were incubated at 37° C. for overnight.

After colonies were recovered on the second day, these filters were placed on filter paper prewetted with denaturing solution for four minutes, then were incubated on top of a boiling water bath for additional four minutes. The filters were then placed on filter paper prewetted with neutralizing solution for four minutes. After excess solution was removed by placing the filters on dry filter papers for one minute, the colony side of the filters were place into Proteinase K solution, incubated at 37° C. for 40–50 minutes. The filters were placed on dry filter papers to dry overnight. DNA was then cross-linked to nylon membrane by UV light treatment.

Colony hybridization was conducted as described by Sambrook, J., Fritsch, E. F. and Maniatis, T., (in Molecular Cloning: A laboratory Manual, 2$^{nd}$ Edition). The following probes were used in colony hybridization:
1. First strand cDNA from the same tissue as the library was made from to remove the most redundant clones.
2. 48–192 most redundant cDNA clones from the same library based on previous sequencing data.
3. 192 most redundant cDNA clones in the entire corn sequence database.
4. A Sal-A20 oligo nucleotide: TCG ACC CAC GCG TCC GAA AAA AAA AAA AAA AAA AAA, listed in SEQ ID NO: 3, removes clones containing a poly A tail but no cDNA.
5. cDNA clones derived from rRNA.

The image of the autoradiography was scanned into computer and the signal intensity and cold colony addresses of each colony was analyzed. Re-arraying of cold-colonies from 384 well plates to 96 well plates was conducted using Q-bot.

EXAMPLE 3

This example describes identification of the gene from a computer homology search.

Gene identities were determined by conducting BLAST (Basic Local Alignment Search Tool; Altschul, S. F., et al., (1990) J. Mol. Biol. 215:403–410) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences were analyzed for similarity to all publicly available DNA sequences contained in the "nr" database using the BLASTN algorithm. The DNA sequences were translated in all reading frames and compared for similarity to all publicly available protein sequences contained in the "nr" database using the BLASTX algorithm (Gish, W. and States, D. J. Nature Genetics 3:266–272 (1993)) provided by the NCBI. In some cases, the sequencing data from two or more clones containing overlapping segments of DNA were used to construct contiguous DNA sequences.

EXAMPLE 4

This example shows a comparison between the polypeptide sequences of the maize Ku80 homologue (SEQ ID NO.

2) and Ku80 homologues from Chinese hamster (SEQ ID NO. 4, Accession No. Q60449), Golden hamster (SEQ ID NO. 5, Accession No. Q60530), mouse (SEQ ID NO. 6, Accession No. P27641), and human (SEQ ID NO. 7, Accession No. P13010) using the PILEUP program of GCG. The maize Ku80 homologue demonstrates a 40–45% similarity and an approximate 25% identity with other eukaryotic Ku80 sequences.

TABLE 1

Amino Acid Sequence Comparison of Plant & Animal Ku80 Homologues

```
                 1                                                    50
SEQ ID NO.4 MAWSANKAAV VLCMDVGVAM GNSFPGEESS FEQAKKVMTM FVQRQVFSES
SEQ ID NO.5 MAWSANKAAV VLCMDVGIAM GNSFPGEESP FEQAKKVMTM FVQRQVFSES
SEQ ID NO.6 MAWSVNKAAV VLCVDVGVAM GNSIPGEESP IEQAKKVMTM FVQRQVFSES
SEQ ID NO.7 ~VRSGNKAAV VLCMDVGFTM SNSIPGIESP FEQAKKVITM FVQRQVFAEN
SEQ ID NO.2 ~~~~~~~~~M ARNREVVILL LDVGPSMHGV LLEVKNVCLT LVHKKLVYNR 51                                                   100
SEQ ID NO.4 KDEIALVLFG TDNTNNALAS E.DQYQNITV HRHLMLPDFD LLEDIESKIQ
SEQ ID NO.5 KDEIALVLFG TDSTENALAS E.DQYQNITV RRHLMLPDFD LLEDIESKIQ
SEQ ID NO.6 KDEIALALYG TDGTDMPLSG K.DQYQNITV CRHLMLPDFD LLEDIGNKIQ
SEQ ID NO.7 KDEIALVLFG TDGTDNPLSG G.DQYQNITV HRHLMLPDFD LLEDIESKIQ
SEQ ID NO.2 SDEVGIVLFG TKGTCNELAK DIGGYKHVTV IHDIKVVDEG TAQALQN.LP 101                                                   150
SEQ ID NO.4 LGSRQADILD ALIVCMDLIQ RE...TIGKK ...FEKKHIE VFTDLSSPFS
SEQ ID NO.5 LGSRQADFLD ALIVCMDLIQ RE...TIGKK ...FGKKHIE VFTDLSSPFS
SEQ ID NO.6 PSSQQADFLD ALIVCMDLIQ RE...TIGKK ...FGKKHIE VFTDLRSPFS
SEQ ID NO.7 PGSQQADFLD ALIVSMDVIQ HE...TIGKK ...FEKRHIE IFTDLSSRFS
SEQ ID NO.2 LGSAPGDFLD SIVVGLDMVI RKFGITKGKR RLCLITSAQE LLRDPPEGTK 151                                                   200
SEQ ID NO.4 QDQLDVIICN LKKSGISLQF FLPFPISKND ETGDRGDGDL GLDHCGPSFP
SEQ ID NO.5 QDQLDVIICN LKKSGISLQF FLPFPISKNN ETGHSGDGDL GLDHRGPSFP
SEQ ID NO.6 KDQLDVIICN LKKCGISLQF FLPFPIDKNG EPGERGDLDS GLDHLKPSFP
SEQ ID NO.7 KSQLDIIIHS LKKCDISLQF FLPFSLGKED GSGDRGDGPF RLGGHGPSFP
SEQ ID NO.2 EDQVDTIADM LKKHNIKMEC II........ .......... ...FREPGVH 201                                                   250
SEQ ID NO.4 QKGITEQQKE GICMVERVMV SLEGEDGLDE IYSFSESLRR LCVFKKIERR
SEQ ID NO.5 QKGVTEQQKE GIRMVERVMV SLEGEDGLDE IYSFSESLRQ LCVFKKIERR
SEQ ID NO.6 QKGLTEQQKE GIRMVTRVML SLEGEDGLDE IYSFSESLRQ LCVFKKIERR
SEQ ID NO.7 LKGITEQQKE GLEIVKMVMI SLEGEDGLDE IYSFSESLRK LCVFKKIERH
SEQ ID NO.2 HNDIMEENDR LLHQFRNRSV AKVIQ..VDN PTSLLGALKT RNVLPVTVFR 251                                                   300
SEQ ID NO.4 SMPWSCQLTI GPDLSIKIVA YKSIVQEKV. ...KKSWIVV DARTLKKEDI
SEQ ID NO.5 SMPWPCQLTI GPDLSIKIVA YKSIVQEKL. ...KKTWVVV DARTLKKEDI
SEQ ID NO.6 SMPWPCQLTI GPNLSIKIVA YKSIVQEKF. ...KKSWVVV DARTLKKEDI
SEQ ID NO.7 SIHWPCRLTI GSNLSIRIAA YKSILQERV. ...KKTWTVV DAKTLKKEDI
SEQ ID NO.2 G.....DLEV NSNFKIKVWV YKKTAEEKFP TLKKYSDKAP PSDKFASHEV 301                                                   350
SEQ ID NO.4 RKETVYCLND DDETEVSKED TIQGFRYGSD IIPFSKVDEE QMKYKSEGKC
SEQ ID NO.5 QKETVYCLND DDETEVSKED TIQGFRYGSD IIPFSKVDEE QMKYKSEGKC
SEQ ID NO.6 QKETVYCLND DDETEVSKED TIQGYRYGSD IIPFSKVDEE QMKYKSEGKC
SEQ ID NO.7 QKETVYCLND DDETEVLKED IIQGFRYGSD IVPFSKVDEE QMKYKSEGKC
SEQ ID NO.2 KVDYEYKSVV EPDKVVPPDQ RIKGYLYGPQ VIPVSNAEWE AVKFKPE.KG 351                                                   400
SEQ ID NO.4 FSVLGFCRSS QVHRRFFMGY QVLKVFAAKD DEAAAVALSS LIHALDELNM
SEQ ID NO.5 FSVLGFCRSS QVHRRFFMGY QVLKVFAAKD DEAAAVALSS LIHALDELNM
SEQ ID NO 6 FSVLGFCKSS QVHRRFFMGH QVLKVFAAKD DEAAAVALSS LVHALDELNM
SEQ ID NO.7 FSVLGFCKSS QVQRRFFMGN QVLKVFAARD DEAAAVALSS LIHALDDLDM
SEQ ID NO.2 VKLLGFTDRS SVPRHQFM.K DVCLFIPEPG NMKASLAVSA IARMMHQMNK 401                                                   450
SEQ ID NO.4 VAIVRYAYDK .RANPQVGVA FPYI...KDS YECLVYVQLP FMEDLRQYMF
SEQ ID NO.5 VAIVRYTYDK .RANPQVGVA FPYI...KDS YECLVYVQLP FMEDLRQYMF
SEQ ID NO.6 VAIVRYAYDK .RSNPQVGVA SLYI...KDA YERLVYVQLP FMEDLRQYMF
SEQ ID NO.7 VAIVRYAYDK .RANPQVGVA FPHI...KHN YECLVYVQLP FMEDLRQYMF
SEQ ID NO.2 VAIVRCVWRQ GQGNVAIGVL TPNISSVNNI QDSFYFNVLP FAEDIREFQF 451                                                   500
SEQ ID NO.4 SSLKN.NKKC TPTEAQLSAI DDLIESMSLV KKSEEEDTIE DLFPTSKIPN
SEQ ID NO.5 SSLKN.NKKC TPTEAQLSAI DDLIESMSLV KKSEEEDTIE DLFPTSKIPN
SEQ ID NO.6 SSLKN.NKKC TPTEAQLSAI DDLIDSMSLV KKNEEEDIVE DLFPASKIPN
SEQ ID NO.7 SSLKN.SKKY APTEAQLNAV DALIDSMSLA KKDEKTDTLE DLFPTTKIPN
SEQ ID NO.2 RSFSSLPSSS QPTEEQQEAA DNLVKMLDLA PPGRE..... .VLKPEFTPN
```

TABLE 1-continued

Amino Acid Sequence Comparison of Plant & Animal Ku80 Homologues

```
              501                                                550
SEQ ID NO.4 PEFQRFFQCL LHRVLHPQER LPPIQQHILN MLNLPTEMKA KCEIPLSKVR
SEQ ID NO.5 PEFQRFFQCL LHRVLHPQER LPPIQQHILN MLDPPTEVKA KCEIPLSKVR
SEQ ID NO.6 PEFQRLYQCL LHRALHLQER LPPIQQHILN IWDPPTEMKQ KCESPPLKVK
SEQ ID NO.7 PRFQRLFQCL LHRALHPREP LPPIQQHIWN MLNPPAEVTT KSQIPLSKIK
SEQ ID NO.2 PILERFYSYL DLKSKQPDAN VPPLERSLRR ITEPDPDVVG QQTQLIQNLS 551                                                600
SEQ ID NO.4 TLFPLTEAVK KKDQVTAQDI FQDIHEEGPA AKKCKTEKEE GHISISSVAE
SEQ ID NO.5 TLFPLTEAVK KKDQVTAQDI FQDNDEEGPA AKKCKMEKEE SHISISSLAE
SEQ ID NO.6 TLFPLTEVIK KKNQVTAQDV FQDNHEEGPA AKKYKTEKEE DHISISSLAE
SEQ ID NO.7 TLFPLIEA.K KKDQVTAQEI FQDNHEDGPT AKKLKTEQGG AHFSVSSLAE
SEQ ID NO.2 KAFVLKENPK KKKART.QDM LAYTGAGDQA KSVEDRVLEN THPSTES...

601                                                650
SEQ ID NO.4 GNVTKVGSVN PVESFRVLVR QKIAS..FEQ ASLQLISHIE QFL.DTNETL
SEQ ID NO.5 GNVTKVGSVN PVENFRVLVR QKIAS..FEE ASLQLISHIE QFL.DTNETL
SEQ ID NO.6 GNITKVGSVN PVENFRFLVR QKIAS..FEE ASLQLISHIE QFL.DTNETL
SEQ ID NO.7 GSVTSVGSVN PAENFRVLVK QKKAS..FEE ASNQLINHIE QFL.DTNETP
SEQ ID NO.2 ..VVAIRDSN PVQDFEAMLA KRSSSTWTQK AIGDMQNYIA ALLQNSSDGG 651                                                700
SEQ ID NO.4 YFMKSMECIK AFREEAIQFS EEQRFNSFLE ALREKVEIKQ LNHFWEIVVQ
SEQ ID NO.S YFMKSMECIK AFREEAIQFS EEQRFNSFLE ALREKVEINE LNHFWEIVVQ
SEQ ID NO.6 YFMKSMDCIK AFREEAIQFS EEQRFNSFLE ALREKVEIKQ LNHFWEIVVQ
SEQ ID NO.7 YFMKSIDCIR AFREEAIKFS EEQRFNNFLK ALQEKVEIKQ LNHFWEIVVQ
SEQ ID NO.2 NYQKALECFA SLRKACIIEQ EPQEFNQFLT NIYERLKEGD AAKFFQLLSS 701                                                750
SEQ ID NO 4 DGVTLITKDE GSGSSVTTEE ATKFLAPKDK AKEDAAGL.E EGGDVDDLLD
SEQ ID NO.5 DGVTLITKDE GPGSSVTTEE ATKFLAPKDK AKEDSAGL.E EGGDVDDLLD
SEQ ID NO.6 DGVTLITKDE APGSSITAEE AKKFLAPKDK AKEDTTGP.E EAGDVDDLLD
SEQ ID NO.7 DGITLITKEE ASGSSVTAEE AKKFLAPKDK PSGDTAAVFE EGGDVDDLLD
SEQ ID NO.2 KNISLINKEE APDSDVTEEM ARSFYLKREK VSQ* ~~~~~ ~~~~~~~~~~

751
SEQ ID NO.4 MI
SEQ ID NO.5 MI
SEQ ID NO.6 MI
SEQ ID NO.7 MI
SEQ ID NO.2 ~~
```

The above examples are provided to illustrate the invention but not to limit its scope. Other variants of the invention will be readily apparent to one of ordinary skill in the art and are encompassed by the appended claims. All publications, patents, patent applications, and computer programs cited herein are hereby incorporated by reference.

---

What is claimed is:

1. An isolated polynucleotide comprising a polynucleotide selected from the group consisting of:
    (a) a polynucleotide having at least 80% sequence identity, as determined by the GAP algorithm under default parameters, over the entire coding region, to the polynucleotide of SEQ ID NO: 1, wherein the polynucleotide encodes a polypeptide with Ku80 activity;
    (b) a polynucleotide encoding the polypeptide of SEQ ID NO: 2;
    (c) a polynucleotide which selectively hybridizes, under stringent hybridization conditions and a wash in 0.1× SSC at 60° C., to the entire length of polynucleotide of SEQ ID NO: 1, wherein the complementary sequence of said polynucleotide encodes a polypeptide with Ku80 activity;
    (d) a polynucleotide of SEQ ID NO: 1; and
    (e) a polynucleotide which is fully complementary to the polynucleotide of (a), (b), (c), or (d).

2. A recombinant expression cassette comprising a member of claim 1 operably linked to a promoter.

3. A host cell transformed with the polynucleotide of claim 1.

4. A transgenic plant comprising the polynucleotide of claim 1.

5. The transgenic plant of claim 4, wherein said plant is a monocot.

6. The transgenic plant of claim 4, wherein said plant is a dicot.

7. The transgenic plant of claim 4, wherein said plant is selected from the group consisting of: maize, soybean, sunflower, sorghum, canola, wheat, alfalfa, cotton, rice, barley, and millet.

8. A transgenic seed from the transgenic plant of claim 4.

9. A method of modulating the level of Ku80 in a plant, comprising:
    (a) introducing into a plant cell a recombinant expression cassette comprising the polynucleotide of claim 1 operably linked to a promoter;
    (b) culturing the plant cell under plant cell growing conditions;
    (c) regenerating a whole plant which possesses the transformed genotype; and
    (c) inducing expression of said polynucleotide for a time sufficient to modulate the level of Ku80 in said transformed plant.

10. The method of claim 9, wherein the plant is selected from the group consisting of: maize, soybean, sunflower, sorghum, canola, wheat, alfalfa, cotton, rice, barley and millet.

11. A transformed plant cell produced by the method of claim 9.

12. A transgenic plant produced by the method of claim 9.

13. A transgenic seed produced by the plant of claim 12.

14. The plant of claim 12, wherein the plant is selected from the group consisting of: maize, soybean, sunflower, sorghum, canola, wheat, alfalfa, cotton, rice, barley, and millet.

* * * * *